US008809263B2

(12) United States Patent
Yeaman et al.

(10) Patent No.: US 8,809,263 B2
(45) Date of Patent: Aug. 19, 2014

(54) ANTI-INFECTIVE HYDROXY-PHENYL-BENZOATES AND METHODS OF USE

(75) Inventors: Michael Yeaman, Redondo Beach, CA (US); Arnold Bayer, Rancho Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/201,447

(22) PCT Filed: Oct. 26, 2009

(86) PCT No.: PCT/US2009/062123
§ 371 (c)(1),
(2), (4) Date: Nov. 3, 2011

(87) PCT Pub. No.: WO2010/048630
PCT Pub. Date: Apr. 29, 2010

(65) Prior Publication Data
US 2012/0040888 A1 Feb. 16, 2012

Related U.S. Application Data

(60) Provisional application No. 61/108,408, filed on Oct. 24, 2008.

(51) Int. Cl.
*A61K 38/00* (2006.01)
*C07K 7/08* (2006.01)

(52) U.S. Cl.
USPC ............... 514/2.7; 514/2.3; 514/2.4; 514/2.6

(58) Field of Classification Search
None
See application file for complete search history.

(56) References Cited

U.S. PATENT DOCUMENTS

| 6,468,967 B1 * | 10/2002 | Oleson et al. ................ 514/2.9 |
| 2008/0194518 A1 | 8/2008 | Mookerjee et al. |
| 2010/0099088 A1 * | 4/2010 | Drummelsmith et al. ........ 435/6 |

FOREIGN PATENT DOCUMENTS

| WO | WO 2006/099325 | 9/2006 |
| WO | WO 2010/036958 | 4/2010 |

OTHER PUBLICATIONS

International Journal of Antimicrobial Agents 24 (2004) 393-396 In vivo efficacy of linezolid in combination with gentamicin for the treatment of experimental endocarditis due to methicillin-resistant *Staphylococcus aureus*. Cedric Jacqueline, et al.*
VISA, hetero-VISA and VRSA: The end of the vancomycin era? John M Conly MD1, B Lynn Johnston MD2 Can J Infect Dis vol. 13 No. 5 Sep./Oct. 2002.*
The significance of MRSA and VRE in chronic wounds Gosbell IB FRACP, FRCPA Primary Intention vol. 10 No. 1 Feb. 2002.*
Comparision of Diflunisal and Aspirin in Long Term treatment of patients with Rheumatoid arthritis. robert turner et al clinical Therayeutics V9 suppl 1986 pp. 37.*
Sedlacek et al American j Kidney Diseases V49 n3 2007 pp. 401-408.*
Nicolau et al., Antimicrobial Agent and Chemitherapy 1995.*
Ruiz et al., Claincal Infectious Diseases 2002.*
Arch Intern Med. Oct. 23, 2006;166(19):2138-44. High-dose vancomycin therapy for methicillin-resistant *Staphylococcus aureus* infections: efficacy and toxicity. Hidayat LK1, Hsu DI, Quist R, Shriner KA, Wong-Beringer A.*
Linezolid Therapy of *Staphylococcus aureus* Experimental Osteomyelitis Robin Patel, Kerryl E. Piper, [ . . . ], and James M. Steckelberg. Antimicrob Agents Chemother. Dec. 2000: 44(12) 3438-3440.*
Bayer et al., "Hperproduction of Alpha-Toxin by *Staphylococcus aureus* Results in Paradoxically Reduced Virulence in Experimental Endocarditis: a Host Defense Role for Platelet Microbicidal Proteins," Infect Immun. 65:4652-60 (1997).
Chan et al., "A randomized trial of asprin on the risk of embolic events in patients with infective endocaritis," J Am Coll Cardiol 42:775-780 (2003).
Cheung et al., "Role of the Distal sarA Promoters in SarA Expression in *Staphylococcus aureus*," Infect Immun. 73:4391-4 (2005).
Cheung et al., "Diminished Virulence of a sar-/agr-Mutant of *Staphylococcus aureus* in the Rabbit Model of Endocarditis," J Clin Invest. 94:1815-22 (1994).
DeVroey, "A double-blind comparison of diflunisal and asprin in the treatment of post-operative pain after episiotomy," Curr Med Res Opin. 5:544-7 (1978).
Dhawan et al. "Thrombin-Induced Platelet Microbicidal Protein Susceptibility Phenotype Influences the Outcome of Oxacillin Prophylaxis and Therapy of Experimental *Staphylococcus aureus* Endocarditis," Antimicrob Agents Chemother. 44:3206-9 (2000).

(Continued)

*Primary Examiner* — Cecilia J Tsang
*Assistant Examiner* — Li Lee
(74) *Attorney, Agent, or Firm* — Jones Day

(57) ABSTRACT

The invention provides a method for preventing or treating a disease caused by an extracellular microorganism, said method comprising systemically administering to a subject in need thereof a prophylactically or therapeutically effective amount of a salicylic acid (SAL) or a SAL analogue. The extracellular microorganism can be of the bacterial genus *Staphylococcus*, for example, *Staphylococcus aureus*. The extracellular microorganism can be a strain that is resistant to at least one antibiotic. The strain can be selected from the group consisting of methycillin-resistant *Staphylococcus aureus* (MRSA), vancomycin-intermediate *Staphylococcus aureus* (VISA) and vancomycin-resistant *Staphylococcus aureus* (VRSA). The invention also provides a method for preventing or treating an infectious disease caused by of methycillin-resistant *Staphylococcus aureus* (MRSA), vancomycin-intermediate *Staphylococcus aureus* (VISA) or vancomycin-resistant *Staphylococcus aureus* (VRSA), comprising systemically coadministering in a synergistic combination to a subject in need thereof prophylactically or therapeutically effective amounts, individually or collectively, of a salicylic acid (SAL) or a SAL analogue and at least one additional antimicrobial agent, for example, vancomycin and/or linezolid.

16 Claims, 23 Drawing Sheets

(56) References Cited

OTHER PUBLICATIONS

Dhawan et al., "Influence of InVitro Susceptibility Phenotype against Thrombin-Induced Platelet Microbicidal Protein on Treatment and Prophylaxis Outcomes of Experimental *Staphylococcus aureus* Endocarditits," J Infect Dis. 180:1561-8 (1999).

Drusano et al., "The Crisis of Resistance: Identifying Drug Exposures to Suppress Amplification of Resistant Mutant Subpopulations," Clin Infect Dis 42:525-32 (2006).

Enright et al., "Multilocus Sequence Typing for Characterization of Methicillin-Resistance and Methicillin-Susceptible Clones of *Staphylococcus aureus*," J Clin Microbiol 38:1008-1015 (2000).

Feil et al., "Recombination and the Population Structures of Bacterial Pathogens," Annu Rev Microbiol 55:561-590 (2001).

Feil et al., "How Clonal is *Staphylococcus aureus*?" J Bacteriol 185:3307-3316 (2003).

Firsov et al., "Testing the mutant selection window hypothesis with *Staphylococcus aureus* exposed to daptomycin and vancomycin in an in vitro dynamic model," J Antimicrob Chemother 58:1185-92 (2006).

Fowler et al., "Potential Association between Hematogenous Complications and Bacterial Genotype in *Staphylococcus aureus* Infection," J. Infect. Dis. 196:738-47 (2007).

Friedman et al., "Genetic Changes That Correlate with Reduced Susceptibility to Daptomycin in *Staphylococcus aureus*," Antimicrob Agents Chemother 50:2137-45 (2006).

Gardete et al., "Role of VraSR in Antibiotic Resistance and Antibiotic-Induced Stress Response in *Staphylococcus aureus*," Antimicrob Agents Chemother 50:3424-34 (2006).

Goerke et al., "Role of *Staphylococcus aureus* Global Regulators sae and σB in Virulence Gene Expression during Device-Related Infection," Infect Immun. 73:3415-21 (2005).

Greene et al., "Adhesion properties of mutants of *Staphylococcus aureus* defective in fibronectin-binding proteins and studies on the expression of fnb genes," Mol Microbiol 17:1143-52 (1995).

Gumbo et al., "Selection of a Moxifloxacin Dose that Suppresses Drug Resistance in *Mycobacterium tuberculosis*, by Use of an In Vitro Pharmacodynamic Infection Model and Mathematical Modeling," J Infect Dis. 190:1642-51 (2004).

Ji et al., "Bacterial Interference Caused by Autoinducing Peptide Variants," Science 276:2027-2030 (1997).

Kang et al., "Pharmacodynamics of RP 59500 Alone and in Combination with Vancomycin against *Staphylococcus aureus* in an In Vitro-Infected Fibrin Clot Model," Antimicrob. Agents Chemother. 39:1505-1511 (1995).

Karlsson et al., "Protection of *Rhesus macaques* against Lethal *Plasmodium knowlesi* Malaria by a Heterologous DNA Priming and Poxvirus Boosting Immunization Regimen," Infect Immun. 70:4239-46 (2002).

Koreen et al., "spa Typing Method for Discriminating among *Staphylococcus aureus* Isolates: Implications for Use of a Single Marker to Detect Genetic Micro-and Macrovariation," J Clin Microbiol 42:792-799 (2004).

Kucukguzel et al., "Synthesis and biological activities of diflunisal hydrazide-hydrazones," European Journal of Medicinal Chemistry 38:1005-1013 (2003).

Kupferwasser et al., "Acetylsalicylic acid reduces vegetation bacterial density, hematogenous bacterial dissemination, and frequency of embolic events in experimental *Staphyloccocus aureus*, endocarditis through antiplatelet and antibacterial effects," Circulation 99:2791-2797 (1999).

Kupferwasser et al., "Salicylic acid atienuates virulence in endovascular infections by targeting global regulatrory pathways in *Staphylococcus aureus*," J Clin Invest 112:222-233 (2003).

Labandeira-Rey et al., "*Staphylococcus aureus* Panton-Valentine Leukocidin Causes Necrotizing Pneumonia," Science 315:1130-3 (2007).

Lyon et al., " Peptide Signaling in *Staphylococcus aureus* and other Gram-positive bacteria," Peptides 25:1389-1403 (2004).

Mercier et al., "Beneficial Influence of Platelets on Antibiotic Efficacy in an In Vitro Model of *Staphylococcus aureus*-Induced Endocarditis," Antimicrob Agents Chemother 48:2551-7 (2004).

Mercier et al., "Influence Platelets and Platelet Microbicidal Protein Susceptibility on the Fate of *Staphylococcus aureus* in an In Vitro Model of Infective Endocardidits," Infect Immun. 68:4699-705 (2000).

Oliveira et al., "Multiplex PCR Strategy for Rapid Identification of Structural Types and Variants of the mec Element in Methicillin-Resistant *Staphylococcus aureus*," Antimicrob Agents Chemother 46:2155-2161 (2002).

Palma et al., "Salicylic Acid Activates Sigma Factor B by rsbU-Dependent and -Independent Mechanisms," J Bacteriol. 188:5896-903 (2006).

Patti et al., "MSCRAMM-Mediated Adherence of Microorganisms to Host Tissues," Annu Rev Microbiol. 48:585-617 (1994).

Peerschke et al., "The contribution of gC1qR/p33 in infection and inflammation," Immunobiology, 212:333-342 (2007).

Proctor et al., "Small colony variants: a pathogenic form of bacteria that facilitates persistent and recurrent infections," Nature (Rev Micro) (4):295-305 (2006).

Riordan et al., "Response of *Staphylococcus aureus* to Salicylate Challenge," Journal of Bacteriology 189(1):220-227 (2007).

Rivas et al., "MSCRAMM-Targeted vaccines and immunotherapy for *Staphylococcal* infection," Curr Opin Drug Discov Devel. 7:223-7 (2004).

Rybak et al., "Pharmacodynamics of RP 59500 (Quinupristin-Dalfopristin) Administered by Intermittent versus Continuous Infusion against *Staphylococcus aureus*-Infected Fibrin-Platelet Clots in an In Vitro Infection Model," Antimicrob. Agents Chemother. 41:1359-1363 (1997).

Saskoulas et al., "Induction of Daptomycin Heterogeneous Susceptibility in *Staphylococcus aureus* by Exposure to Vancomycin," Antimicrob Agents Chemother 50:1581-5 (2006).

Saskoulas et al., "Adaptation of Mehicillin-Resistant *Staphylococcus aureus* in the Face of Vancomycin Therapy," Clin Infect Dis 42:540-50 (2006).

Saskoulas et al., "*Staphylococcus aureus* Accessory Gene Regulator (agr) Group II: Is There A Relationship to the Development of Intermediate-Level Glycopeptide Resistance?" J Infect Dis 187:929-38 (2003).

Spratt, "Multilocus sequence typing: molecular typing of bacterial pathogens in an era of rapid DNA sequencing and the Internet," Curr Opin Microbiol 2:312-316 (1999).

Taha et al., "Asprin to prevent growth of vegetations and cerebral emboli in infective endocarditis," J. Intern. Med., 231:543-546 (1992).

Tam et al., "Impact of Drug-Exposure Intensity and Duration of Therapy on the Emergence of *Staphylococcus aureus* Resistance to a Quinolone Antimicrobial," J Infect. Dis. 195:1818-27 (2007).

Voyich et al., "Is Panton-Valentine Leukocidin the Major Virulence Determinant in Community-Associated Methicillin-Resistant *Staphylococcus aureus* Disease?" J Infect Dis. 1994:1761-70 (2006).

Wagner et al., "Bismuth subsalicylate in the treatment of H2 blocker resistant duodenal ulcers: role of Helicobacter pylori," Gut 33:179-183 (1992).

Wann et al., "The Fibronectin-binding MSCRAMM FnbpA of *Staphylococcus aureus* Is a Bifunctional Protein that also Binds to Fibrinogen," J Biol Chem. 275:13863-71 (2000).

Weidenmaier et al., "DltABCD- and MprF-Mediated Cell Envelope Modifications of *Staphylococcus aureus* Confer Resistance to Platelet Microbicidal Proteins and Contribute to Virulence in a Rabbit Endocarditis Mode, Infect Immun. 73:8033-8 (2005).

Weidenmaier et al., "Lack of Wall Teichoic Acids in *Staphylococcus aureus* Leads to Reduced Interactions with Endothelial Cells and to Attenuated Virulence in a Rabbit Model of Endocarditis,"J Infect Dis 191:1771-7 (2005).

Xiong et al., "In Vitro Antibacterial Activities of Platelet Microbicidal Protein and Neutrophil Defensin against *Staphylococcus aureus* Are Influenced by Antibiotics Differing in Mechanism of Action," Antimicrob Agents Chemother. 43:1111-7 (1999).

(56) References Cited

OTHER PUBLICATIONS

Xiong et al., "Real-Time In Vivo Bioluminescent Imaging for Evaluating the Efficacy of Antibiotics in a Rat *Staphylococcus aureus* Endocarditis Model," Antimicrob Agents Chemother. 49:380-7 (2005).

Xiong et al., "Impacts of sarA and agr in *Staphylococcus aureus* Strain Newman on Fibronectin-Binding Protein A Gene Expression and Fibronectin Adherence Capacity In Vitro and in Experimental Infective Endocarditis," Infect Immun. 72:1832-6 (2004).

Xiong et al., "Inhibition of Intracellular Macromolecular Synthesis in *Staphylococcus aureus* by Thrombin-Induced Platelet Microbicidal Proteins," J Infect Dis. 185:348-56 (2002).

Xiong et al., "Activation and Transcriptional Interaction between agr RNAII and RNAIII in *Staphylococcus aureus* In Vitro and in an Experimental Endocarditis Model," J Infect Dis. 186:668-77 (2002).

Xiong et al., "Regulation of *Staphylococcus aureus* α-Toxin Gene(hla) Expression by agr, sarA and sae In Vitro and in Experimental Infective Endocarditis," J Infect Dis. 194:1267-75 (2006).

Yeaman et al., "*Staphylococcus aureus*, platelets, and the heart," Curr Infect Dis Rep. 2:281-298 (2000).

Yeaman et al., "Synthetic Peptides That Exert Antimicrobial Activities in Whole Blood and Blood-Derived Matrices," Antimicrob Agents Chemother 46(12): 3883-91 (2002).

Yeaman et al., "Code among Chaos: Immunorelativity and the AEGIS Model of Antimicrobial Peptides," ASM News 71:21-7 (2005).

Yeaman et al., "Modular determinants of antimicrobial activity in platelet factor-4 family kinocidins," Biochem Biophy Acta. 1768:609-19 (2007).

Yeaman et al., "Unifying themes in host defence effector polypeptides," Nature (Rev Micro) 5:727-40 (2007).

Yeaman et al., "Mechanisms of Antimicrobial Peptide Action and Resistance," Pharmacol Rev 55(1):27-55 (2003).

Yount et al., "Platelet Microbicidal Protein 1: Structural Themes of a Multifunctional Antimicrobial Peptide," Antimicrob Agents Chemother 48:4395-404 (2004).

Yount et al., "Structural correlates of antimicrobial efficacy in IL-8 and related human kinocidins," Biochem. Biophys. Acta (in press) (2007).

Yount et al., "Structural congruence among membrane-active host defense polypeptides of diverse phylogeny," Biochem. Biophys. Acta 1758:1373-1386 (2006).

Yount et al., "Multidimensional signatures in antimicrobial peptides," Proc Natl Aced Sci U S A 101(19):7363-8 (2004).

Yount et al., "Immunocontinuum: Perspectives in Antimicrobial Peptide Mechanisms of Action and Resistance," Protein Pept Lett 12(1):49-67 (2005).

Zhao et al., "Restricting the Selection of Antibiotic-Resistant Mutant Bacteria: Measurement and Potential Use of the Mutant Selection Window," J Infect Dis. 185:561-5 (2002).

\* cited by examiner

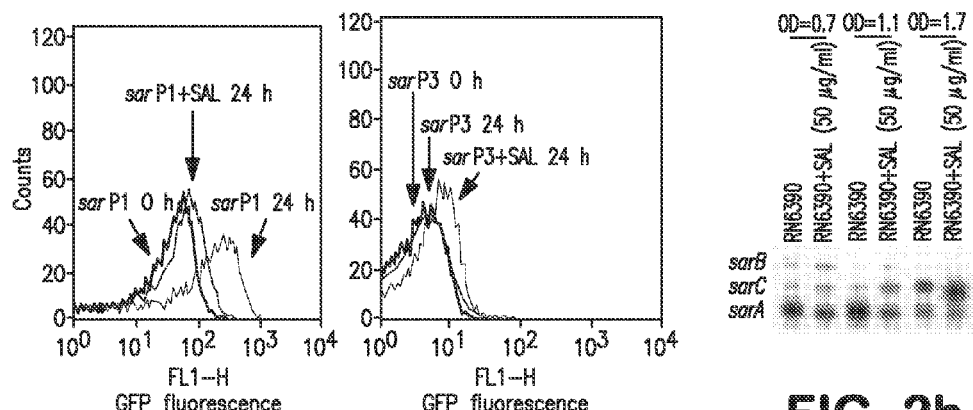
FIG. 2a
FIG. 2b
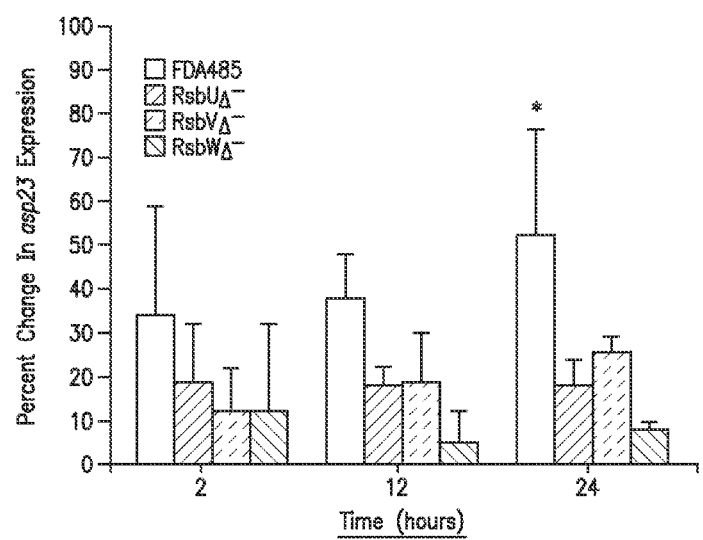
FIG. 3

|  | Laboratory isolates | | Clinical isolates | |
|---|---|---|---|---|
|  | SAL, 30 μg/ml | SAL, 50 μg/ml | SAL, 30 μg/ml | SAL, 50 μg/ml |
| Fibronectin binding | -35.9% ± 6.5%[A] | -54.5% ± 5.1%[B] | -28.9% ± 3.5%[B] | -51.4% ± 2.0%[B] |
| Fibrinogen binding | -35.4% ± 5.2%[A] | -55.1% ± 4.9%[B] | -32.4% ± 2.1%[B] | -53.4% ± 2.9%[B] |
| Hemolysis | -48% ± 4%[B] | -62% ± 5%[B] | -33% ± 13%[A] | -54% ± 12%[B] |
| Thrombolysis | -32% ± 4%[A] | -45% ± 2%[B] | -30% ± 6%[A] | -48% ± 9%[B] |

FIG. 10

|  |  | | Vegetation Bacterial Counts | | |
|---|---|---|---|---|---|
|  | n | Vegetation Weight, mg | $\log_{10}$ CFU/vegetation | $\log_{10}$ CFU/g | Kidney Bacterial Counts $\log_{10}$ CFU/g |
| Control | 11 | 74±41 | 7.11±1.24 | 8.36±1.03 | 6.42±1.65 |
| ASA 4 mg kg$^{-1}$ d$^{-1}$ | 8 | 36±30 | 4.97±1.45 | 6.59±1.77 | 4.92±1.29 |
| ASA 8 mg kg$^{-1}$ d$^{-1}$ | 11 | 19±8* | 4.35±1.26* | 6.13±1.37* | 5.24±1.32 |
| ASA 12 mg kg$^{-1}$ d$^{-1}$ | 10 | 55±22 | 6.17±1.59 | 7.48±1.69 | 6.05±1.38 |

*$P<0.05$ vs control.

FIG. 11

|  | Treatment (Log CFU/g±SD) | | Relapse (Log CFU/g±SD) | |
|---|---|---|---|---|
| Regimen | Vegetations | Kidneys | Vegetation | Kidney |
| Control | 8.4 ± 0.9 | 7.8 ± 1.6 | - | - |
| ASA (3mg/kg) | 7.4 ± 0.2 | 7.4 ± 0.2 | - | - |
| ASA (8mg/kg) | 6.7 ± 0.9* | 6.6 ± 0.9* | 7.2 ± 0.6 | 7.1 ± 0.8 |
| Vancomycin (7.5mg/kg bid) | 5.2 ± 1.1* | 5.0 ± 1.2* | 7.1 ± 0.7 | 6.8 ± 1.0 |
| ASA (3) + Van | 5.3 ± 1.1 | 4.9 ± 1.3 | - | - |
| ASA (8) + Van | 4.1 ± 0.9** | 3.9 ± 1.0** | 6.4 ± 0.9 | 6.3 ± 1.0 |

Key: *$p<0.05$ vs. controls; **$p<0.05$ vs. controls and $p<0.05$ vs. vancomycin and ASA alone

FIG. 12

| Strain | Source | Vancomycin | Daptomycin | *arg* type | *sigB* status |
|---|---|---|---|---|---|
| USA300 | CA-MRSA; sequenced | VSSA | DSSA | I | + |
| MW2 | Clinical; sequenced | VSSA | DSSA | IIII | + |
| MU-50 | Clinical; sequenced | VISA | DSSA | II | + |
| DSSA-parent | Clinical; Cubist | VSSA | DSSA | II | + |
| DNSA-mutant | Clinical; Cubist | VISA | SNSA | II | + |

FIG. 13

| MRSA Gene | Rationale | Reference |
|---|---|---|
| sarA | prototypic member of sar regulon | Xiong et al. J Infect Dis. 2006 194:1267-75; Xiong et al. Infect Immun. 2004 72:1832-6. Dunman et al. J Bacteriol. 2001 183:7341-53; Chien et al. J Biol Chem. 1999 274:37169-76. |
| ARG (RNAIII) | prototypic member of arg regulon | Xiong et al. J Infect Dis. 2002 186:668-77; Xiong et al. J Infect Dis. 2006 194:1267-75; Xiong et al. Infect Immun. 2004 72:1832-6. |
| sigB | regulatory impact of sarA and arg | Entenza et al. Infect Immun. 2005 73:990-8; Berger-Bachi and Projan, J Bacteriol. 2004 186:4085-99; |
| mprF | involved in mechanism of peptide antibiotic resistance | Friedman et al. Antimicrob Agents Chemother. 2006 50:2137-45. |
| yycFG | involved in mechanism of peptide antibiotic resistance | Friedman et al. Antimicrob Agents Chemother. 2006 50:2137-45. |
| vraSR | implicated in mechanism of peptide antibiotic resistance | Gardete et al. Antimicrob Agents Chemother. 2006 50:3424-34 |
| hla | encodes α-hemolysin; prototypic virulence factor in IE | Herbert et al. Infect Immun. 2001 69:2996-3003; Vandenesch et al. J Bacteriol. 1991 173:6313-20 |
| fnbA | encodes fibronectin BP A; prototypic virulence factor in IE | Greene et al. Mol Microbiol. 1995 17:1143-52; Patti et al. Annu Rev Microbiol. 1994 48:585-617. |
| pvl | encodes PV-leukocidin; potential virulence factor/surrogate | Voyich et al. J Infect Dis. 2006 194:1761-70; Labandeira-Rey et al. Science. 2007 315:1130-3 |

FIG. 14

Investigational Compounds
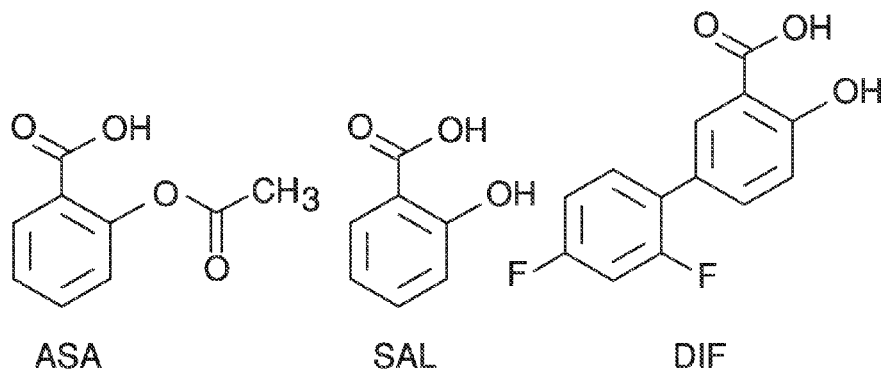
FIG. 15

S. aureus Strains Investigated

| Strain | Description |
|---|---|
| SH1000 | 8325-4; functional *rsbU*; MSSA |
| USA300 | Clinical (FPR 3757); CA-MRSA |
| SH100 *agr-* | *agr-* mutant of SH1000 |
| RN6390 | 8325-4 *rsbU* derivative |
| FDA486 | WT strain with intact *rsbU* |
| ALC2128 | *rsbU-* mutant of FDA486 |
| ALC2129 | *rsbV-* mutant of FDA486 |
| ALC2130 | *rsbW-* mutant of FDA486 |
| USA400 | MW2; CA-MRSA |
| COL | MRSA strain |
| COL *agr-* | *agr-* mutant of COL |
| ATCC29213 | CLSI standard strain |

FIG. 16

Genotypic/Phenotypic Markers

- Pilot study findings:
    No significant static or cidal effects *in vitro*
    Modulatory effects occur in log-phase growth
    GTA or SUA no significant effects *in vitro*

- RT qPCR of gene expression (n ≥ 3)

- Hemolysin/protease elaboration

| Regulatory | Exoprotein | Resistance |
|---|---|---|
| RNAIII (agr) | hla (α-tox) | dltA |
| sarA | sspA (V8) | mprF |
| sigB | | yycG |
| | | vraR |

FIG. 17

Net Hemolysin Expression

Percent of Control

| STRAIN | ASA | SAL | GTA | SUA | DIF |
|---|---|---|---|---|---|
| SH1000 | 102.97[a] | 93.13 | 109.51 | 95.70 | 74.83* |
| USA300 | 98.54 | 98.60 | 90.61 | 78.14 | 52.46* |

* $P < 0.05$
a: (TREAT PLATE RATIO[b]) / (CONTROL PLATE RATIO) X 100; Control = 100%
b: [(HEMOLYTIC AREA) - (COLONY AREA] / (COLONY AREA)

FIG. 23

Net Protease Expression

Percent of Control

| STRAIN | ASA | SAL | GTA | SUA | DIF |
|---|---|---|---|---|---|
| SH1000 | 99.48[a] | 98.75 | 78.48 | 93.73 | $\leq 5$[†] |
| USA300 | 93.19 | 77.39 | 105.42 | 110.38 | $\leq 5$[†] |

[†] $P<0.01$
a: (DRUG PLATE RATIO[b]) / (CONTROL PLATE RATIO) X 100; Control = 100%
b: [(PROTEOLYTIC AREA) - (COLONY AREA] / (COLONY AREA)

FIG. 25

ANTI-INFECTIVE HYDROXY-PHENYL-BENZOATES AND METHODS OF USE

CROSS-REFERENCE TO RELATED APPLICATIONS

This application is a U.S. National Stage Application under U.S.C. §371 of International Patent Application No. PCT/US2009/062123, filed Oct. 26, 2009, which claims the benefit of priority to U.S. Provisional Application Ser. No. 61/108,408, filed Oct. 24, 2008.

BACKGROUND OF THE INVENTION

Invasive infections by Staphylococcus aureus are now common and life-threatening. As methicillin-resistant (MRSA) or vancomycin-refractory (VISA, VRSA) strains are leading community-acquired and nosocomial pathogens, invasive S. aureus infections now have attributable mortalities approaching 40%-50%, even with modern therapeutics. Costs associated with such infections now exceed $2 billion per year in the US alone. Such a clear and present threat to public health emphasizes the urgency to address this unmet medical need. Yet, remarkably little is known of pharmacologic approaches to minimize resistance or enhance antibiotic efficacy vs. MRSA. As an alternative to the time and cost of developing new anti-staphylococcal antibiotics, there is a need to discover adjunctive combinations that mitigate resistance and optimize therapeutic outcomes to serious or life threatening bacterial infections, including methicillin-resistant SA (MRSA), that are increasingly refractory to most if not all forms of conventional antimicrobial therapy (pan-resistant). The present invention meets this need and provides related advantages.

SUMMARY OF INVENTION

The invention provides a method for preventing or treating a disease caused by an extracellular microorganism, said method comprising systemically administering to a subject in need thereof a prophylactically or therapeutically effective amount of a salicylic acid (SAL) or a SAL analogue. The extracellular microorganism can be of the bacterial genus Staphylococcus, for example, Staphylococcus aureus. The extracellular microorganism can be a strain that is resistant to at least one antibiotic. The strain can be selected from the group consisting of methycillin-resistant Staphylococcus aureus (MRSA), vancomycin-intermediate Staphylococcus aureus (VISA) and vancomycin-resistant Staphylococcus aureus (VRSA). The invention also provides a method for preventing or treating an infectious disease caused by of methycillin-resistant Staphylococcus aureus (MRSA), vancomycin-intermediate Staphylococcus aureus (VISA) or vancomycin-resistant Staphylococcus aureus (VRSA), comprising systemically co-administering in a synergistic combination to a subject in need thereof prophylactically or therapeutically effective amounts, individually or collectively, of a salicylic acid (SAL) or a SAL analogue and at least one additional antimicrobial agent, for example, vancomycin and/or linezolid.

BRIEF DESCRIPTION OF THE DRAWINGS

FIG. 2 shows that SAL treatment modulates expression of sar regulon components sarA, sarB, and sarC within S. aureus. GFP outcomes (2A) are in very close agreement with transcriptional expression results from Northern analyses (2B).

FIG. 3 shows that SAL induces sigB expression (as measured by increases in asp23 expression) in S. aureus.

FIG. 10 depicts how SAL treatment mitigates ligand adhesion and α-toxin production among laboratory and clinical S. aureus strains.

FIG. 11 depicts how aspirin (ASA) benefits outcomes in a rabbit model of S. aureus IE.

FIG. 12 depicts the beneficial impact of aspirin on vancomycin therapy of MRSA in the rabbit model of IE. Key: *p<0.05 vs. controls; **p<0.05 vs. controls and p<0.05 vs. vancomycin and ASA alone.

FIG. 13 depicts strategic MRSA strain panel to be prioritized in the methods of the invention.

FIG. 14 shows lists strategic target genes to be assessed for SAL-antibiotic impact.

FIG. 15 shows candidate compounds for practicing the methods of the invention.

FIG. 16 shows examples of S. aureus strains suitable for practicing in the methods of the invention.

FIG. 17 shows genotypic and phenotypic markers utilized in the invention.

FIG. 23 shows net hemolytic expression in S. aureus strains SH1000 and USA300 as a result of addition of ASA, SAL, GTA, SUA and DIF as percent of control.

FIG. 25 shows net protease expression in S. aureus strains SH1000 and USA300 as a result of addition of ASA, SAL, GTA, SUA and DIF as percent of control.

DETAILED DESCRIPTION OF THE INVENTION

Figure 1A:
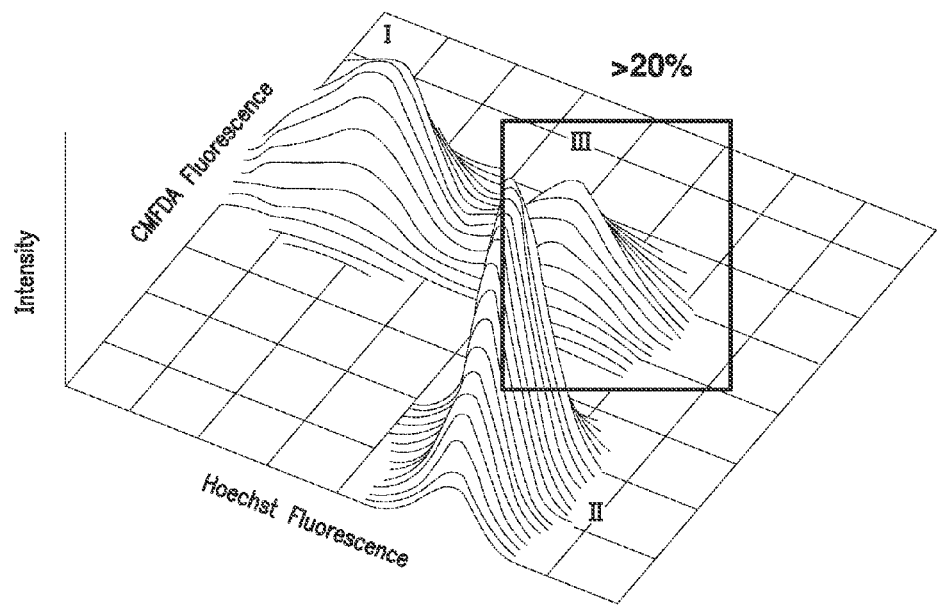
FIG. 1 shows that SAL mitigates the binding of S. aureus to human platelets (1B), as compared to organisms prior to SAL exposure (1A).

The present invention is based, in part, on the discovery that salicylic acid (SAL), a major biometabolite of aspirin, modulates *S. aureus* phenotypic and genotypic determinants to mitigate resistance and enhance efficacy of anti-staphylococcal antibiotics. The invention provides methods of mitigating resistance and enhancing efficacy of anti-staphylococcal antibiotics. The invention also provides methods for predicting antimicrobial activities of agents not presently recognized to have such antimicrobial activities, based upon structure-activity correlates. The invention is based, in part, on the surprising discovery that salicylate analogues of the chemical structure containing one or more halogenated fluorophenyl moieties have unexpected capacities with regard to mitigating resistance and enhancing efficacy of anti-staphylococcal antibiotics. For example, the chemical 5-(2,4-difluorophenyl)-2-hydroxy-benzoic acid, generic clinical drug name, Diflunisal [DIF] or Dolobid, unexpectedly and surprisingly has markedly greater anti-SA activities than SAL. Traditionally, DIF is considered to be of clinical use as a nonsteroidal anti-inflammatory drug (NSAID), having analgesic and anti-inflammatory effects. Originally, DIF was marketed by Merck, but has not been widely used in the United States. It is believed to be of greatest clinical use as an NSAID in Australia. As disclosed herein, the physicochemical moieties in DIF and analogous compounds perturb virulence factor regulation and expression in SA. The perturbation occurs due to the relatively specific inhibition of agr, RNAIII, or sigB and related regulatory systems in SA. As disclosed herein, the virulence factors controlled by these regulators is suppressed, and such suppression translates to improved outcomes.

The present invention is based, in part, on the discovery that salicylic acid (SAL; a major biometabolite of aspirin) modulates *S. aureus* phenotypic and genotypic determinants to mitigate resistance and enhance efficacy of anti-staphylococcal antibiotics. The invention ptovides PK-PD systems to model and therapeutically translate the beneficial impact of salicylates on vancomycin or daptomycin efficacy. Strategic, genetically-defined *S. aureus* strains can be used to elucidate the quantitative relationships between SAL exposure and phenotypic or genotypic resistance to vancomycin or daptomycin in vitro.

The methods described herein include an integrated approach to quantify the impact of SAL on the MRSA mutation prevention concentration (MPC) and mutation selection window (MSW), and assessment of SAL str uctural analogues for enhanced down-modulation of *S. aureus* resistance to peptide antibiotics.

This invention provides methods of adjunctive SAL-peptide antibiotic therapy to mitigate resistance and improve outcomes of life-threatening invasive MRSA infections in humans.

The invention further provides an ex vivo model of *S. aureus* infection simulating fluid and tissue phases of human cardiovascular infection will be used to define kinetic relationships between SAL, vancomycin, or daptomycin that mitigate phenotypic and genotypic resistance profiles in MRSA. This controlled system simulates targeted and dynamic peak and trough antibiotic concentrations, and affords pharmacokinetic (PK) optimization. SAL mitigation of antibiotic resistance will be assessed in MRSA residing in distinct contexts: circulating bacteria versus bacteria embedded within infected vegetations.

The purpose of the invention addresses existing or novel molecules for developed as novel antiinfective (principally anti-SA or anti-MRSA) agents to act alone or in combination with other antiinfective therapies or strategies. A main focus of the utility of the invention would be treatment or prevention of life-threatening infections caused by pathogens resistant to existing therapies, or to enhance the efficacy of existing antimicrobial agents against SA or other organisms.

The method of claim 1, wherein the extracellular microorganism is a species of a genus selected from the group consisting of bacterial genera *Staphylococcus, Enterococcus, Escherichia, Streptococcus, Campylobacter, Salmonella, Helicobacter, Bacillus, Clostridium, Corynebacterium, Chlamydia, Coxilla, Ehrlichia, Francisella, Pasteurella, Brucella, Proteus, Klebsiella, Enterobacter, Tropheryma, Acinetobacter, Aeromonas, Alcaligenes, Capnocytophaga, Erysipelothrix, Listeria*, and *Yersinia*.

The method of claim 2, wherein said species is selected from the group consisting of *Staphylococcus aureus, Staphylococcus epidermidis, Enterococcus faecalis, Enterococcus faecium, Salmonella typhi, Salmonella typhimurium, Salmonella enterica, Escherichia coli, Streptococcus pneumoniae, Streptococcus pyogenes, Streptococcus agalactiae, Helicobacter pylori*, and *Campylobacter jejuni*.

Based on structure-activity correlates, the invention provides method for the discovery of novel compounds with significant anti-SA or other antimicrobial activities alone or in combination with antibiotics, due to similar or greater effects on suppression of virulence factors in MRSA or other human pathogenic microbes.

DIF and other structural analogues of SAL achieve anti-SA efficacy in vitro and in vivo by suppression of regulons and the virulence factors they control. In particular, the regulatory genes agr, RNAIII, and sigB, the well-characterized virulence factors hla ($\alpha$-hemolysin) and sspA (V8 protease), and certain antibiotic resistance sensor or effector genes such as vraA, dltA, mprF, or yycG/F are abnormally regulated or expressed in the presence of DIF or analogues thereof (see attached materials). DIF and related compounds can be used as an anti-infective strategy alone or in combination with conventional antibiotics to suppress virulence and/or enhance efficacy of antimicrobial regimens, particularly against resistant organisms.

The invention is further based on the discovery of a relatively narrow concentration range that effects the desirable anti-SA activities, without untoward effects on the host or the pathogen.

SAL, DIF, and certain structural analogues thereof structurally or functionally mimic auto-inducing peptides generated by SA to govern regulation of genes in adaptation of the organism that allow it to survive and cause infection in the host. This process, termed quorum-sensing, is integral to the ability of the organism to sense excess organism density, depletion of nutrients, or injurious immune context, and counter-regulate gene expression. The result of this process is the tight regulation of virulence factor expression for optimal survival of the organism in vivo. Thus, inhibition of the capability by DIF or related analogues prevents a normal adaptive capability of the organism, making it susceptible to immune mechanisms as well as antimicrobial therapy.

Prior art antibiotics employ mechanisms that inhibit essential functions of microbes, resulting in static growth or killing. In contrast, SAL, DIF or analogues thereof have only modest effects on organism growth, and do not cause organism death. Rather, they suppress regulatory and effector genes that encode adaptive and virulence proteins needed to cause infection. SALs, DIF, or derivatives thereof can be to be developed as novel antiinfective agents to act against human pathogens that are refractory to existing anti-infectives.

Invasive infections caused by *Staphylococcus aureus* are life-threatening conditions now reported at an alarming frequency. Presently, *S. aureus* is the most common cause of skin 3-6 and endovascular infections, including infective endocarditis (IE) and device-related infections, and the second most common agent of bacteremia. The incidence of invasive *S. aureus* continues to increase rapidly. For example, IE due to *S. aureus* occurs in up to 10,000 new patients per year in the United States, and 1-year mortality remains near 40% despite advances in anti-staphylococcal therapy and surgical methods. Even more troubling has been the global explosion in *S. aureus* antibiotic resistance. In just the past decade alone, MRSA infections have become epidemic in communities among the US and worldwide. Reports of multiple pan-antibiotic resistant *S. aureus*, including resistance to vancomycin, daptomycin, and linezolid, illustrate the daunting scope of this problem. Unacceptably, the mortality due to invasive *S. aureus* infections such as IE has remained unchanged in the last two decades. Finally, invasive MRSA infections affect many risk populations, including those in: i) jails; ii) public health facilities; iii) long term care facilities; iv) dialysis centers; and v) pediatric practices. Although most of these infections have been of skin and soft tissue origin, an increasing proportion (up to 10%) involves complicated blood stream infections.

Methicillin-resistance in nosocomial and community-acquired isolates of *S. aureus* has been steadily increasing, and now approaches national rates between 30-60% among patients in intensive care units. In recent reports, the median length of hospital stay for nosocomial infections was 12 days for MRSA, versus 4 days for methicillin-susceptible *S. aureus* (MSSA), and 23 days for MRSA versus 14 days for MSSA in patients with surgical site infections. The rise in hospital cost is significantly higher for treatment of MRSA than for MSSA infections, and has a greater mortality due to nosocomial MRSA infections than MSSA. Further complicating these issues is the limited availability of effective antimicrobial therapy against MRSA. Vancomycin has been a mainstay of therapy for decades; yet its role in therapy has raised questions. Vancomycin failure against *S. aureus* having minimum inhibition concentrations (MICs) of 2 µg/ml has occurred, despite proactive and aggressive dosing. This problem is compounded by increased prevalence of *S. aureus* strains with MICs of 2 µg/ml. Moreover, most strains exhibiting vancomycin MICs of ≥2 µg/ml also display heteroresistance to vancomycin (hVISA). Even in the currently susceptible range established by the CLSI, infections caused by hVISA have been linked to vancomycin failure. Several centers have now reported the vancomycin MIC upward shift ("MIC creep"). For example, a leading center in North Carolina evaluated MRSA isolates from 2001 and 2005 and demonstrated that the proportion of strains with vancomycin MIC >1 µg/ml increased from 0% in 2001 to 7% in 2005. Rates as high as 54% of strains with vancomycin MICs of ≥2 µg/ml among nosocomial MRSA isolates have been reported, raising new concerns for vancomycin efficacy. In addition, there are several recent case reports of daptomycin-resistance emerging during therapy associated with clinical failures.

A link exists between vancomycin failure and *S. aureus* accessory gene regulator (agr) function. In *S. aureus*, the agr regulon controls exoprotein, exotoxin, and adhesin expression; many of these proteins are established virulence factors. Four predominant agr types predominate, and specific agr genotype strains appear to be associated with particular infectious syndromes in certain locales. In the US, VISA strains in agr group II, and mutations or defects in this operon, are correlated with decreased vancomycin efficacy. Loss of agr function appears to offer a survival advantage for the organism. The prevalence of the agr group types can vary in different hospitals, and agr group II is not an absolute requirement for the development of vancomycin resistance. However, a majority of MRSA isolates in U.S. hospitals are agr type II.

Suboptimal vancomycin dosing drives development of VISA strains. A correlation exists between vancomycin dosing and resistance in the setting of agr locus dysfunction; roughly 48% of hospital-acquired MRSA are defective in agr function. Agr dysfunction may result in hypo- or hyper-expression of one or more virulence factors. In *S. aureus*, vancomycin resistance manifests as two principal types: VISA and VRSA.

In VISA strains, no individual genetic defect has been identified, but rather appears to involve complex metabolic perturbations which result in excess D-alanine residues in the pentapeptide bridge; abnormal muropeptide species; and thick cell walls. These abnormalities appear to be responsible for reduced access of vancomycin via the cell wall to reach its target. In contrast, VRSA strains contain a vancomycin-resistance determinant (commonly vanA) that is apparently acquired from vancomycin-resistant enterococci, and encodes an aberrant pentapeptide target for vancomycin (D-alanine-D-lactate or D-alanine-D-serine) instead of a native D-alanine-D-alanine. This putative pseudo-target prevents binding of vancomycin to its mechanistic target. "Hetero-VISA" isolates are defined as those with vancomycin MICs within the CLSI-defined susceptible range (≤2 ug/ml), but which possess resistant clones upon population analyses. Such strains are associated with clinical treatment failures. Specific genes are potential candidate effectors in daptomycin resistance. For example, genes correlating with daptomycin resistance phenotypes include mprF and yycF/G; variations ranging from point to frameshift mutations have been seen and reported in these gene loci. Paradoxically, mutations in mprF yield a "gain in function", affording excess translocation of positively charged phospholipids (lysyl-phosphotidyl glycerol [LPG]) from the inner to the outer cell membrane bilayer. These events yield an increased net positive charge of the bacterial cell surface, postulated to enable charge repulsion of the calciumdecorated active form of daptomycin. Also, mutations in these genes proceed in a coordinated, sequential manner, with mprF being an initial mutation, followed in-turn by mutations in yycF/G.

Aspirin and its major human biometabolite, SAL, can influence responsivity of MRSA to antibiotic therapy in experimental model systems. This effect appears to be due at least in-part to SAL modulation of genes integral to the MRSA "resistome" adaptations active in antibiotic resistance, and the "virulon" for endovascular pathogenesis.

The invention provides methods of treating a microbial infection by administering to an individual in need thereof an agent such as, for example, a SAL analogue, such as DIF or a structure function analogue of SAL. The invention also provides methods to enhance efficacy or suppress emergence of antibiotic resistance in MRSA by administering to an individual in need thereof an agent such as, for example, SAL, a SAL analogue, such as DIF or a structure function analogue of SAL.

State-of-the art pharmacologic modeling in relevant in vitro, ex vivo, and in vivo systems was performed to define the essential relationships for therapeutic optimization of antimicrobial efficacy and dampening of antibiotic resistance versus MRSA or other pathogens.

As disclosed herein, SAL, DIF, or analogues thereof enhance efficacies of standard antimicrobial therapy. In the rabbit model of *S. aureus* IE, two intravenous (iv) aspirin dose regimens designed to encompass those used in a previous aspirin-alone efficacy study (4 or 8 mg/kg/d) were employed. Animals received aspirin alone, vancomycin alone at a low dose regimen (7.5 mg/kg bid iv), or the two agents combined. Treatment was only for 2d, based on the rationale that as the in vivo effects of vancomycin are traditionally slow in onset, maximal disclosure of any synergistic effect of the two compounds may emerge at this early time point.

Aspirin dosed at 8 mg/kg/d (but not 4 mg/kg/d) or vancomycin significantly reduced bacterial counts in vegetations and kidneys. Importantly, aspirin (8 mg/kg/d) combined with vancomycin further decreased target tissue counts by at least 1 log 10 cfu/g. DIF+vancomycin or other analogue+antibiotic combination regimens have not been evaluated in discriminatory animal models of SA or MRSA infection. The results obtained underscore the potential for combined SAL-, DIF-, or like analogue-plus antibiotic synergy in vivo to optimize efficacy and suppress emergence of antimicrobial resistance. In vitro studies showed that DIF is approximately 10-fold more effective than SAL in suppressing virulence factor regulation or expression in MRSA, including the highly publicized epidemic MRSA strain, USA300.

Examples of infectious diseases treatable by the present invention are those as to which the subject to be treated can benefit from a systemic administration of SAL analogues and include, but are not limited to, those caused by extracellular bacteria of the species of *Staphylococcus*, such as *Staphylococcus aureus*, *Staphylococcus epidermidis*, and the like; of *Enterococcus*, such as *Enterococcus faecalis*, *Enterococcus faecium*, and the like; of *Salmonella*, such as *Salmonella typhi*, *Salmonella typhimurium*, *Salmonella enterica*, and the like; of *Escherichia*, such as *Escherichia coli*, and the like; of *Streptococcus*, such as *Streptococcus pneumoniae*, *Streptococcus pyogenes*, *Streptococcus agalactiae*, and the like; of *Helicobacter*, such as *Helicobacter pylori*, and the like; of *Campylobacter*, such as *Campylobacter jejuni*, and the like; as well as the species of genera, *Yersinia*, *Chlamydia*, *Coxilla*, *Ehrlichia*, *Francisella*, *Legionella*, *Pasteurella*, *Brucella*, *Proteus*, *Klebsiella*, *Enterobacter*, *Tropheryma*, *Acinetobacter*, *Aeromonas*, *Alcaligenes*, *Capnocytophaga*, *Bacillus*, *Clostridium*, *Corynebacterium*, *Erysipelothrix*, *Listeria* and the like. Examples of infectious diseases treatable by the present invention also include infections caused by fungi, such as *Candida albicans*, *Microsporum canis*, *Sporothrix schenckii*, *Trichophyton rubrum*, *Trichophyton mentagrophytes*, *Malassezia furfur*, *Pityriasis versicolor*, *Exophiala werneckii*, *Trichosporon beigelii*, *Coccidioides immitis*, *Blastomyces dermatitidis*, *Aspergillus fumigatus*, *Epidermophyton* spp., *Fusarium* spp., *Zygomyces* spp., *Rhizopus* spp. *Mucor* spp., and so forth.

SAL analogues can be administered by any methods that result in systemic distribution or delivery of the SAL analogues and include oral administration and parenteral administration, such as intravenous administration, intramuscular administration, subcutaneous administration, intraperitoneal administration, and the like. In certain infections, oral administration of SAL analogues provides not only systemic distribution/delivery of the SAL analogues to the affected area but also a direct contact of the compounds with the causative microorganisms in the affected area, such as within the digestive tracts. Thus, oral administration of the SAL analogues is especially useful in preventing or treating digestive tract infections caused by various microorganisms, including, but not limited to, *Staphylococcus aureus*, *Enterococcus faecalis*, *Enterococcus faecium*, *Salmonella typhi*, *Salmonella typhimurium*, *Salmonella enterica*, *Escherichia coli*, *Campylobacter jejuni*, *Clostridium difficile*, *Clostridium perfringens*, and the like. *Helicobacter pylori* that causes gastric and duodenal ulcers, gastritis, duodenitis, and gastric cancer, is also a good target for the methods of the present invention.

Furthermore, the methods of the present invention can be applied to preventing or treating infectious diseases caused by microorganisms that are resistant to at least one antimicrobial agent other than SAL analogues. The term "antimicrobial agent" used herein refers to any naturally or synthetically derived agent that kills microorganisms or inhibits the growth thereof, directly or indirectly, and includes conventional antibiotics as well as synthetic chemotherapeutic agents, such as sulfonamides, isoniazid, ethambutol, AZT, synthetic peptide antibiotics, and the like. Thus, in a specific embodiment, the infectious diseases preventable or treatable by the present invention are caused by antimicrobial-resistant strains of microorganisms mentioned above, in particular, of *Staphylococcus aureus*, *Enterococcus faecium*, *Enterococcus faecalis*, *E. coli*, *Salmonella typhi*, *Campylobacter jejuni*, *Klebsiella pneumoniae*, *Neisseria gonorrhoeae*, *Candida albicans*, and the like. More specifically, such antimicrobial-resistant organisms include methicillin-resistant *Staphylococcus aureus* (MRSA), vancomycin-resistant enterococci (VRE), ampicillin-resistant *E. coli* (e.g., *E. coli* O157:H7), fluoroquinolone-resistant *Salmonella* thyphi, ceftazidime-resistant *Klebsiella pneumoniae*, fluoroquinolone-resistant *Neisseria gonorrhoeae*, and the like. The methods of the present invention can be applied to any other pathogenic microorganisms which have become resistant to antimicrobial agents other than gallium, as far as they are dependent on iron for their growth and survival.

SAL analogues to be used in the present invention can be formulated in conventional manner using one or more pharmaceutically acceptable carriers or excipients. As used herein the phrase "pharmaceutically acceptable carriers or excipients" is intended to include any and all solvents, dispersion media, coatings, isotonic and absorption delaying agents, and the like, which are compatible with pharmaceutical administration. The use of various pharmaceutically acceptable carriers or excipients for pharmaceutically active substances is well known in the art.

The therapeutically effective amount (i.e., dosage) of a SAL analogue can vary based on the nature and severity of the infection to be treated, the types of etiologic microorganism, the location of the affected area, the method of administration, the age and immunological background of a subject, the types of SAL analogues used, as well as other factors apparent to those skilled in the art. Typically, a therapeutically effective amount of a SAL analogue can be that amount which gives a concentration at the affected area of the body or in blood plasma, of at least about 1 µM, at least about 50 µM, at least about 100 µM, at least about 500 µM, at least about 1 mM, at least about 10 mM, at least about 50 mM, at least about 100 mM, at least about 200 mM, up to about 500 mM. Due to gallium's low toxicity, the amount may be liberally increased to more than 500 mM but less than that amount which causes any toxicity. For the methods of the present invention, what is contemplated is administration of the SAL analogues at dosages of, at least about 10 mg/m2/day, at least about 50 mg/m$^2$/day, at least about 100 mg/m$^2$/day, at least about 200 mg/m$^2$/day, at least about 300 mg/m$^2$/day, at least about 500 mg/m$^2$/day, at least about 600 mg m$^2$/day, at least about 700 mg/m$^2$/day, or at least about 800 mg/m$^2$/day, but less than that dosage which causes any toxicity.

The prophylactically effective amount of a SAL analogue may be that amount sufficient to prevent a disease or disorder associated with pathogenic microorganisms and may vary based on the location of the affected area, the types and the number of the pathogenic organisms in the area, the types of SAL analogue to be used, as well as on the methods of application and other factors apparent to those skilled in the art. Typically, the prophylactically effective amount of a SAL analogue may be that amount which gives a concentration at the affected area of the body or in blood plasma, of at least about 0.1 .mu.M, at least about 50 μM, at least about 100 μM, at least about 500 μM, at least about 1 mM, at least about 10 mM, at least about 50 mM, at least about 100 mM, up to about 200 mM. Again, the amount of a SAL analogue for prophylactic purposes may be liberally increased to more than 200 mM but less than the amount that causes any toxicity.

In another aspect, the present invention provides a method for preventing and/or treating infectious diseases caused by extracellular microorganisms, said method comprising co-administering to a subject in need thereof prophylactically or therapeutically effective amounts, individually or collectively, of a SAL analogue and at least one additional antimicrobial agent. The term "co-administration" or "co-administering" used herein refers to the administration of SAL analogue and at least one additional antimicrobial agent either sequentially in any order or simultaneously, by the same administration method or a combination of different administration methods, for example, by an intravenous administration of the SAL analogue and an oral administration of the additional antimicrobial agent, or vice versa. Such co-administration of one or more additional antimicrobial agents together with the SAL analogue is especially beneficial because the drugs attack the causative organisms by non-overlapping, completely different mechanisms, and/or because the development of antimicrobial resistance in the organisms may involve different mechanisms for the different antimicrobial agents, thereby causing nearly complete eradication of the organisms, by the drugs themselves or in combination with the actions by the host's own immune system and reducing or eliminating the chance for the causative organisms to develop resistance to the drugs. Furthermore, thanks to the low toxicity of gallium, by increasing the dosage of gallium, a combination therapy can reduce the dosage of an additional antimicrobial agent to an amount less than that required when the latter is used alone, thereby reducing adverse effects of the latter. Moreover, co-administration of a SAL analogue and an additional antimicrobial agent may result in a synergistic effect and, thus, require less dosages than those required when each is used alone.

Examples of antibacterial agents include, but not by way of limitation, those in the classes of penicillins, including amipicillin, flucloxacillin, dicloxacillin, methicillin, ticarcillin, piperacillin, carbapenems, mecillinams, and the like; cephems, including cephalosporin and cephamycins; sulfonamides; aminoglycosides, including amikacin, gentamicin, kanamycin, neomycin, netilmicin, paromomycin, streptomycin, tobramycin, apramycin, and the like; chloramphenicol; tetracyclines, including chlortetracycline, oxytetracycline, demeclocycline, doxycycline, lymecycline, meclocycline, methacycline, minocycline, rolitetracycline, and the like; macrolides, including erythromycin, azithromycin, clarithromycin, dirithromycin, roxithromycin, carbomycin A, josamycin, iktasamycin, oleandomycin, spiramycin, troleandomycin, tylosin/tylocine, telithromycin, cethromycin, ansamycin, and the like; lincosamides, including lincomycin, clindamycin, and the like; streptogramins, including mikamycins, pristinamycins, oestreomycins, virginiamycins, and the like; glycopeptides, including acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin, and the like; rifamycins, including rifampicin, rifabutin, rifapentine, and the like; nitroimidazoles, including metronidazole, nitrothiazoles, and the like; quinolones, including nalidixic acid, cinoxacin, flumequine, oxolinic acid, piromidic acid, pipemidic acid, ciprofloxacin, enoxacin, fleroxacin, lomefloxacin, nadifloxacin, norfloxacin, ofloxacin, pefloxacin rufloxacin, balofloxacin, grepafloxacin, levofloxacin, pazufloxacin mesilate, sparfloxacin, temafloxacin, tosufloxacin, clinafloxacin, gemifloxacin, moxifloxacin, gatifloxacin, sitafloxacin, trovafloxacin, and the like; dihydrofolate reductase inhibitors, including trimethoprim; oxazolidinones, including linezolid, eperezolid, and the like; lipopeptides, including gramicidins, polymyxins, surfactin, and the like; and analogs, salts and derivatives thereof. Examples of antifungal agents include, but are not limited to, polyenes, such as amphotericin, nystatin, pimaricin, and the like; azole drugs, such as fluconazole, itraconazole, ketoco, and the like; allylamine and morpholine drugs, such as naftifine, terbinafine, amorolfine, and the like; antimetabolite antifungal drugs, such as 5-fluorocytosine, and the like; and analogs, salts and derivatives thereof.

Which antimicrobial agent should be used in combination with the SAL, DIF, or analogues thereof in any given infection can be determined by various simple and routine methods known to one skilled in the art. For example, an infectious microorganism isolated from a patient can be tested for its sensitivity to various antimicrobial agents using a standardized disk-diffusion method (e.g., Kirby-Bauer disk-diffusion method). Briefly, in this method, an appropriate agar plate is uniformly inoculated with the test organism and paper disks impregnated with predetermined concentrations of different antibiotics are placed on the agar surface. After incubation, the diameter of a circular zone, around the disks, in which the growth of the organism is inhibited is measured. The diameter of the inhibition zone is a function of the amount of the antibiotic in the disk as well as the susceptibility of the organism to the antibiotic. The antibiotics to which the organism shows susceptibility can be used for a combination treatment with the SAL analogues. Other examples of antibiotic susceptibility tests include, but are not limited to, a broth tube dilution method for determining Minimum Inhibitory Concentration (MIC) and Minimum Bactericidal Concentration (MBC) of a given antimicrobial agent against a given organism.

Thus, in a specific embodiment, an infection caused by MRSA can be treated by co-administration of SAL or a SAL analogue and vancomycin or linezolid (e.g., ZyVox™ by Pfizer, N.Y.) to a subject in need thereof. Vancomycin and Zyvox™, respectively, are currently used as the antibiotics of choice to treat MRSA infections. Likewise, in another specific embodiment, an infection caused by VRE can be treated by co-administration of a SAL, DIF, or analogues thereof and linezolid. In yet another specific embodiment, an infection or a disease/disorder (e.g., peptic ulcers, gastritis, duodenitis, gastric cancer, and the like) caused by *Helicobacter pylori* can be treated by co-administration of SAL, DIF or analogues thereof and clarithromycin, amoxicillin and/or metronidazole. Other agents that directly or indirectly inhibit or suppress the growth of *Helicobacter pylori* can be also co-administered with the SAL, DIF or analogues thereof. Such agents include, but are not limited to, proton pump inhibitors, such as omeprazole that is currently used together with clarithromycin and amoxicillin in triple therapy for peptic ulcers; and urease inhibitors, such as fluorofamide, acetohydroxamic acid, certain divalent metal ions, including Zn, Cu, Co, and Mn, and the like; as well as other agents, such as bismuth compounds (e.g., bismuth subsalicylate) that not only protect the stomach lining by coating the latter, but also suppress *H. pylori* growth (S. Wagner et al., 1992, "Bismuth subsalicylate in the treatment of H2 blocker resistant duodenal ulcers: role of *Helicobacter pylori*", Gut 33:179-183).

In another aspect, the present invention provides a kit comprising one or more vials containing a SAL analogue and one or more additional antimicrobial agents.

As used herein, "SAL analogue" refers to an structural or functional analogue of salicylic acid. SAL analogues include, for example, Diflunisal and other hydroxyl-phenyl-benzoates. Salicylate analogues of the chemical structure containing one or more halogenated fluorophenyl moieties, for example, 5-(2,4-difluorophenyl)-2-hydroxy-benzoic acid are particularly useful for practicing the claimed methods. SAL analogues structurally or functionally mimic auto-inducing peptides generated by *Staphylococcus aureus* to govern regulation of genes in adaptation of the organism that allow it to survive and cause infection in the host.

As used herein, "salicylate" encompasses any salt or ester of salicylic acid. The salicylates used as drugs for their analgesic, antipyretic and anti-inflammatory effects include aspirin (acetylsalicylic acid, ASA), methyl salicylate and sodium salicylate.

Extracellular microorganisms that have developed resistance to antimicrobial drugs. Common examples of these organisms include, for example, MRSA, VRE (vancomycin-resistant enterococci), ESBLs (extended-spectrum beta-lactamases) (which are resistant to cephalosporins and monobactams) and PRSP (penicillin-resistant *Streptococcus pneumoniae*). Of these, MRSA and VRE are the most commonly encountered multidrug-resistant organisms in patients residing in non-hospital healthcare facilities, such as nursing homes and other long-term care facilities. PRSP are more common in patients seeking care in outpatient settings such as physicians' offices and clinics, especially in pediatric settings.

*Staphylococcus aureus*, often simply referred to simply as "staph", are bacteria commonly found on the skin and in the noses of healthy people. Occasionally, staph can cause infection; staph bacteria are one of the most common causes of skin infections in the United States. Most of these infections are minor (such as pimples, boils, and other skin conditions) and most can be treated without antimicrobial agents (also known as antibiotics or antibacterial agents). However, staph bacteria can also cause serious and sometimes fatal infections (such as bloodstream infections, surgical wound infections, and pneumonia). In the past, most serious staph bacterial infections were treated with a type of antimicrobial agent related to penicillin. Over the past 50 years, treatment of these infections has become more difficult because staph bacteria have become resistant to various antimicrobial agents, including the commonly used penicillin-related antibiotics.

VISA and VRSA are specific types of antimicrobial-resistant staph bacteria. While most staph bacteria are susceptible to the antimicrobial agent vancomycin some have developed resistance. VISA and VRSA cannot be successfully treated with vancomycin because these organisms are no longer susceptibile to vancomycin. However, to date, all VISA and VRSA isolates have been susceptible to other Food and Drug Administration (FDA) approved drugs.

Staph bacteria are classified as VISA or VRSA based on laboratory tests. Laboratories perform tests to determine if staph bacteria are resistant to antimicrobial agents that might be used for treatment of infections. For vancomycin and other antimicrobial agents, laboratories determine how much of the agent it requires to inhibit the growth of the organism in a test tube. The result of the test is usually expressed as a minimum inhibitory concentration (MIC) or the minimum amount of antimicrobial agent that inhibits bacterial growth in the test tube. Therefore, staph bacteria are classified as VISA if the MIC for vancomycin is 4-8 µg/ml, and classified as VRSA if the vancomycin MIC is >16 µg/ml.

Individuals targeted by the methods of the invention are those individuals with several underlying health conditions (such as diabetes and kidney disease), previous infections with methicillin-resistant *Staphylococcus aureus* (MRSA), tubes going into their bodies (such as intravenous [IV] catheters), recent hospitalizations, and recent exposure to vancomycin and other antimicrobial agents.

The invention provides a method for preventing or treating a disease caused by an extracellular microorganism, said method comprising systemically administering to a subject in need thereof a prophylactically or therapeutically effective amount of a salicylic acid (SAL) or a SAL analogue. The extracellular microorganism can be of the bacterial genus *Staphylococcus*, for example, *Staphylococcus aureus*. The extracellular microorganism can be a strain that is resistant to at least one antibiotic. The strain can be selected from the group consisting of methycillin-resistant *Staphylococcus aureus* (MRSA), vancomycin-intermediate *Staphylococcus aureus* (VISA) and vancomycin-resistant *Staphylococcus aureus* (VRSA).

The invention provides a method for preventing or treating an infectious disease caused by MRSA, comprising systemically co-administering in a synergistic combination to a subject in need thereof prophylactically or therapeutically effective amounts, individually or collectively, of a salicylic acid (SAL) or a SAL analogue and at least one additional antimicrobial agent, for example, vancomycin and/or linezolid.

The invention provides a method for preventing or treating an infectious disease caused by VRE, comprising systemically co-administering to a subject in need thereof prophylactically or therapeutically effective amounts, individually or collectively, of a salicylic acid (SAL) or a SAL analogue and at least one additional antimicrobial agent.

Disease caused by an extracellular organism can be selected from the groups consisting of skin infection, soft tissue infection, blood stream infection, bacteremia, pneumonia, osteomyelitis, acute endocarditis, myocarditis, pericarditis, cerebritis, meningitis, antibiotic-associated diarrhea, scalded skin syndrome, abscesses formation and combinations thereof. The disease targeted by the methods of the invention can further be selected from the group consisting of skin infection, soft tissue infection, blood stream infection, and combinations thereof, and the mixture is topically administered to the patient. A therapeutic mixture can be administered from one to twelve or twenty-four times daily as well as continuously. Admisitration can be intravenous, topical or by any other method known to those skilled in the art Throughout this application various publications are referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also provided within the definition of the invention provided herein. Accordingly, the following examples are intended to illustrate but not limit the present invention.

EXAMPLE I

DIF and SAL Modulate agr and Subordinate Gene Expression in Early Log Phase Growth and at Sublethal Concentrations In vitro This example demonstrates that DIF and SAL modulated agr and subordinate gene expression in early log phase growth and at sublethal concentrations in vitro. Such suppression arrests virulence determinant expression and benefits efficacy of anti-SA therapy in vivo.

Coordinated virulence gene expression is critical to *S. aureus* (SA) pathogenesis. A narrow salicylate (SAL) concentration range reduces SA virulence in animal models of infection. This example demonstrates the ability of SAL or analogues to modulate SA gene expression as a basis for anti-SA efficacy in vivo.

SAL or its parent compound acetylsalicylic acid (ASA), its biometabolites gentisic acid (GTA) and salicyluric acid (SCU), or its structural analogue diflunisal (DIF) were tested for efficacy (25 μg/ml) in modulating expression of SA regulon (sigB, sarA, agr RNAIII), exoprotein (hla, sspA), or putative antibiotic resistance (mprF, vraR) genes in vitro. Gene expression was quantified by realtime PCR in distinct growth phases; two SA strains were studied to test potential strain specificities: SH1000 (MSSA), USA300 (MRSA). Hemolysin or antibiotic resistance phenotypes were compared to gene expression.

In early log phase (2-4 hr) in SH1000, DIF caused a >20-fold suppression of agr RNAIII, hla, and vraR. Likewise in USA300, DIF suppressed agr RNAIII, hla, mprF, and sspA. Hemolysis phenotypes were suppressed in parallel to hla. SAL and ASA exhibited limited modulation of gene expression or hemolysis, but GTA or SCU did not alter gene expression. DIF prevented increases in ciprofloxacin MIC vs. both strains. No compound attenuated sigB or sarA expression in log phase, or any gene in stationary phase, nor was lethal to either strain.

EXAMPLE II

Salicylates Enhance In vivo Efficacy of Vancomycin in Established *S. aureus* IE This example demonstrates that aspirin treatment improves antibiotic therapeutic outcomes within a rigorous efficacy challenge model, rabbit IE.

A rabbit model of *S. aureus* IE was previously employed involving two intravenous (iv) aspirin dose-regimens designed to encompass those used in a prior aspirin-alone efficacy study (4 or 8 mg/kg/d). Kupferwasser et al. J Clin Invest. 2003 112:222-33; Kupferwasser et al. Circulation. 1999 99:2791-7. In this follow-up study, animals received aspirin alone, vancomycin alone at a lowdose regimen (7.5 mg/kg bid iv), or the two agents combined. Treatment was only for 2d, based upon the rationale that as the in vivo effects of vancomycin are traditionally slow in onset, maximal disclosure of any synergistic effect of the two compounds emerge at this early time point. Aspirin dosed at 8 mg/kg/d (but not 4 mg/kg/d) or vancomycin significantly reduces bacterial counts in vegetations and kidneys. Importantly, aspirin (8 mg/kg/d) combined with vancomycin further decreased target tissue counts by at least 1 $\log_{10}$ cfu/g. Neither of the regimens fully prevented relapse of infection (4d post-therapy) after this short-course treatment. These results confirm the potential for combined SAL-antibiotic synergy in vivo.

EXAMPLE III

Aspirin and SAL Modify Phenotypic or Genotypic Profiles in *S. aureus* to Benefit Antibiotic Therapy Through Increased Efficacy and/or Reduced Resistance Emergence This example demonstrates that SAL benefits antibiotic therapy through increased efficacy and/or reduced resistance emergence and causes these effects by modulating genetic responses required for antibiotic resistance and virulence.

SAL does not Directly Inhibit *S. aureus* Growth at Clinically-Relevant Concentrations.

The in vitro MICs of aspirin and SAL against three well-known laboratory strains of *S. aureus*: ISP479C, Newman and COL were tested. A range of drug concentrations was tested, from human-equivalent therapeutic range for the anti-platelet aggregation effects of aspirin (10-50 ug/ml), up to supra-physiologic concentrations (8 mg/ml). Over this large concentration range, no substantial growth inhibition was observed. Moreover, there was no measurable change in baseline media pH over this concentration range. These data affirmed a relative lack of in vitro growth inhibitory impact, and predicted that selection of aspirin-SAL resistance would be unlikely at human-equivalent PK-PDs.

SAL Mitigates *S. aureus* Adhesion to Human Ligands Involved in Endovascular Pathogenesis Induction of endovascular infections is linked to the microbial binding to relevant vascular damage sites. The in vitro capacity of *S. aureus* strains to bind to ligands for surface adhesins (i.e. MSCRAMMs), platelets, platelet-fibrin matrices, and endothelial cells in vitro, in the presence of absence of overnight culture in SAL (50 μg/ml) was tested as follows:

A. MSCRAMMs. Fibrinogen and fibronectin play key roles as ligands for *S. aureus* binding to cellular docking sites (e.g., platelets and endothelial cells), as well as bridging molecules that facilitate these same interactions in which additional factors are operative (e.g., gC1qR-platelet or endothelial cell binding). Peerschke and Ghebrehiwet, Immunobiology. 2007 212:333-42 The capacity of SAL at two clinically-relevant serum levels (30 and 50 μg/ml) to influence *S. aureus*-tofibrinogen or -fibronectin binding in solid-phase assays was investigated using 9 individual strains, including well-known MSSA laboratory strains, ISP479C, ISP479R, RN6390 and Newman, MRSA lab strains 67-0 and COL, and three bacteremic isolates from patients with MSSA IE. Importantly, significant anti-adhesive effects of SAL were observed to an equivalent extent in all nine strains; thus, data are presented as a composite of the 9-strain data set (FIG. 10). Of note, there were similar and significant reductions in fibrinogen and fibronectin binding among both laboratory and clinical strains pre-exposed to SAL, in a SAL dose-dependent manner.

FIG. 10 shows that SAL treatment mitigates ligand adhesion and α-toxin production among laboratory and clinical *S. aureus* strains. Mean reduction (±SD) vs. control (100%). Data are composite results of laboratory *S. aureus* RN6390, COL, Newman, and ISP479C, and clinical MRSA 67-0, 6850, Duke 28, Duke 153, and Duke 237. Data and methods are found in Wann et al. J Biol. Chem. 2000 275:13863-71. Key: A P<0.005; B<P 0.001.

B. Platelet-Fibrin Matrices. A solid-phase plate assay was used to quantify the impact of SAL on the ability of *S. aureus* to adhere to fibrin and platelet-fibrin matrices. Platelet-rich (PRP) or platelet-free plasma (PFP) from control animals or those given a single-dose of aspirin iv (8 mg/kg) 5 hr prior to plasma isolation, were used to generate such matrices. Significant reductions were observed in binding to each matrix type after organism pre-exposure to SAL in vitro. Kupferwasser et al. Circulation. 1999 99:2791-7. These strains bound equally to control matrices and those constructed from aspirin-treated animals (data not shown).

Figure 1B:
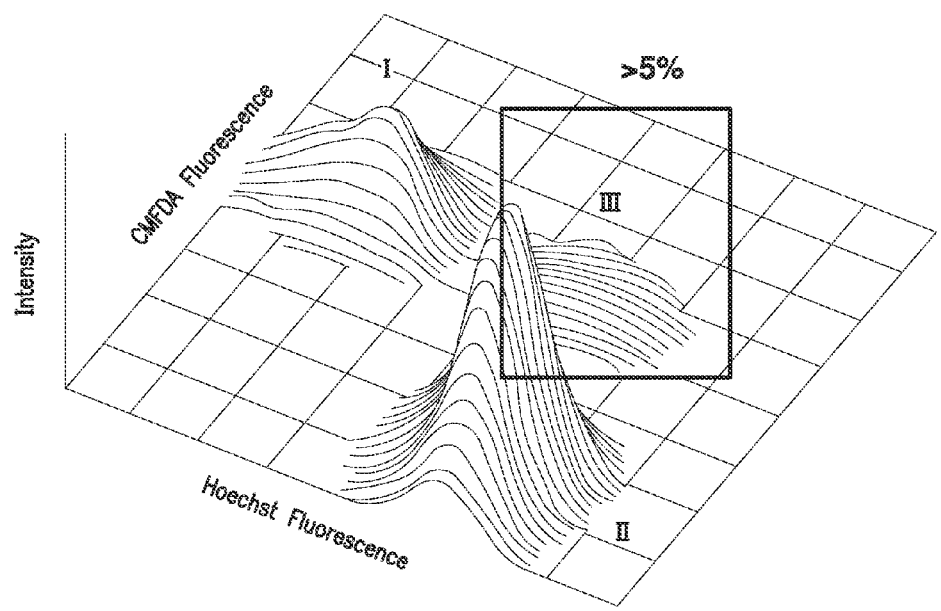

C. Platelets. Platelet adhesion was investigated by flow cytometry in liquid phase, using Hoechst-labeled *S. aureus* cells and CMFDA-labeled human platelets. The proportion of dual-labeled particles (indicative of bacterial-platelet adhesion) was quantified in the presence and absence of SAL pre-exposures (FIG. 1; insets). Pre-incubation of *S. aureus* (ISP479C) in SAL significantly reduced its capacity to bind to platelets. Kupferwasser et al. Circulation. 1999 99:2791-7

D. Vascular Endothelial Cells. In vitro adhesion of *S. aureus* to human vascular endothelial cells (HUVECs) was assayed as done previously. Kupferwasser et al. Circulation. 1999 99:2791-7. Pre-incubation in SAL reduced the binding efficiency of ISP479C adherence to these cells by ~50%. Kupferwasser et al. Circulation. 1999 99:2791-7.

SAL Reduces Production of Exotoxins by *S. aureus*

Exotoxins and exoenzymes elaborated by *S. aureus* play critical roles in endovascular pathogenesis. For example, the classic exotoxin α-toxin, targets key cell types abundant in contexts of endovascular damage, such as platelets, red blood cells and endothelial cells. This toxin is believed to facilitate organism dissemination from such locations. Similarly, proteases (e.g., V8 protease) are felt to be important in remodeling bacterial surface-expressed protein adhesins, and foster the transition from the colonization-to-dissemination phases of infection. To examine the effects of SAL on α-toxin production, the impact of this agent on the capacity of stationary phase *S. aureus* supernates to lyse red cells or platelets (marker for α-toxin elaboration; FIG. 10) was assayed. Using the same strains as for the ligand binding assays above, we demonstrated that SAL reduced thrombolysis and hemolysis, each in a dose-dependent manner. Western blot assays were conducted to further confirm the dampening effects of SAL on α-toxin production. As seen in FIG. 10, SAL reduced α-toxin elaboration in laboratory and clinical *S. aureus* strains. Paradoxically, protease activity in these supernatants was also increased up to five-fold in the presence of SAL. However, inclusion of α2-macroglobulin (a global protease inhibitor) did not prevent the down-modulating impact of SAL on fibronectin or fibrinogen binding, suggesting this effect was independent of changes in protease expression.

Reduced ligand binding and α-toxin production, with a concomitant increase in protease production, pointed to down-regulatory effects of SAL on the global regulator, sarA. Normally, the sar regulon represses proteases, and activates surface adhesin genes and α-toxin expression. Wann et al. J Biol Chem. 2000 275:13863-71 To test this regulatory paradigm, we assessed the impact of SAL upon two key sarA-repressible genes, lipase and protein A. Kupferwasser et al. J Clin Invest. 2003 112:222-33. Lipase activity was increased ~2.6 fold in the presence of SAL, and protein A expression increased by ~20%. In parallel, using a GFP promoter:reporter fusion system, protein A gene expression (spa) was increased in the presence of SAL. This pattern of data suggests a sarA-repressive network underlying the inhibitory mechanism(s) of SAL. The proposed studies confirm that SAL modulates sar and agr regulons in this respect.

Epistasis Analyses Suggest SAL Modulates Definable Gene Regulation of MRSA In vitro Potential pathways of SAL-mediated gene networks emerged from the net results of the phenotypic assays. Likely candidates for inclusion in this network included the global regulator, sarA, and downstream effector genes, including those involved in fibronectin and fibrinogen binding (e.g. fnbA and clfA) and α-toxin elaboration (e.g., hla). As SAL is a weak acid, we postulated that the stress-response sigB system may also be active in such response pathways. Moreover, one of the three major sar promoters (P3) is sigB-dependent, and contributes to net SarA elaboration. Kupferwasser et al. J Clin Invest. 2003 112:222-33' Cheung and Manna, Infect Immun. 2005 73:4391-4.

Further, the effects of another key global regulator, agr, can oppose selected functions of sarA (e.g., repress adhesin gene expression) or complement them (e.g., induce α-toxin gene expression). Cheung et al., FEMS Immunol Med Microbiol. 2004 40:1-9. In light of this dual role, the agr two-component regulator was also examined in our epistasis investigations with SAL. To test potential genetic impacts of SAL on pathways above, we constructed a series of promoter:reporter plasmid fusions, in which a red-shifted variant of GFP (GFPuvr) served as the reporter. The advantage of this variant is its ability to be detected and quantified in vitro and in vivo by standard argon laser-based flow cytometry. Xiong et al. J Infect Dis. 2006 194:1267-75; Xiong et al. Infect Immun. 2004 72:1832-6. These constructs included: sarA:GFP(P1), sarC:GFP, agr RNAIII:GFP; fnbA:GFP; asp23:GFP (a surrogate for sigB expression) and hla:GFP. Depending on the study goals, fusion plasmids were in distinct genetic background strains. In several of the investigations below, a chemically unrelated non-steroidal anti-inflammatory agent, diclofenac (DICL), was used as a control:

A. SAL Reduces Expression of sarA, agr, and hla, but Increases sigB Expression.

Both SAL and DICL reduced agr expression in vitro, and in a dose-dependent manner (SAL at 25 or 50 µg/ml; DICL, 2.5 or 5 µg/ml). All GFP outcomes were confirmed by Northern blots, affirming the reductions in sarA expression. In contrast, and of great interest, expression of the sigB-dependent gene sarC was found to be concurrently up-regulated (FIG. 2). As both agr and sarA positively control expression of hla, GFP studies were conducted to assess the impact of SAL and DICL on hla expression. Results confirm SAL significantly reduced hla expression; Western blots verified a SAL doseependent reduction in Hla protein production.

FIG. 2 shows that SAL treatment modulates expression of sar regulon components sarA, sarB, and sarC within *S. aureus*. This composite figure depicts the simultaneous impact of SAL in down-regulating sarA (P1), while up-regulating sarC (P3). This pattern of data strongly predicts that SAL mitigation of antibiotic resistance and/or virulence genes involves induction of the sigB regulon and its coordinate influences. Note that the GFP outcomes (2A) are in very close agreement with transcriptional expression results from Northern analyses (2B).

B. SAL Induces sigB Expression by rsbU-Dependent and rsbU—Independent Mechanisms.

Data above indicated SALmediated, sigB hyper-expression; yet it was important to further define the genetic determinants underlying this effect. As above, SAL mitigated virulon expression in 8325-4 lineage strains (e.g., ISP479; RN6390) which possess a natural 11-bp deletion in their rsbU sensor module of the sigB operon, rendering them sigBdefective. Palma et al. J Bacteriol. 2006 188:5896-903. These findings suggested that SAL may activate the sigB operon via a rsbU-rsbV-rsbW-sigB regulatory pathway, and by an rsbU bypass mechanism. As shown in FIG. 3, sigB hyper-expression (per increased asp23 expression) induced by SAL was seen in rsbU and rsbV mutants of the sigB-intact strain, FDA 486. Palma et al. J Bacteriol. 2006 188:5896-903. Further evidence that sigB acts in SAL-induced anti-S. aureus effects derive from α-toxin expression studies. Using Hla protein production as a readout, we found that deleting the sigB operon in strain ALC1001 (RN6390=parent) abrogated the suppressive effect of SAL, but was reversed by complementation of the sigB knockout in strain 1497 (data not shown). Kupferwasser et al. J Clin Invest. 2003 112:222-33.

FIG. 3 shows that SAL induces sigB expression (as measured by increases in asp23 expression) in S. aureus. Note that deleting any of the sigB-regulon components (rsbU/V/W) leads to reduction of the SAL effect. These data indicate that SAL modulates gene expression in MRSA via sigB dependent as well as -independent pathways. These and other results disclosed herein show that antibiotic resistance and virulence genes are modulated by SAL, yielding improved treatment efficacy. *Significant difference (P<0.05) versus other outcomes.

These data confirm that aspirin and SAL beneficially impact antibiotic efficacy by mitigating resistance and virulence gene regulation and expression in MRSA MRSA.

SAL Mitigates Adaptive Responses of the MRSA Resistome.

There are no published data that SAL can directly modulate vancomycin or daptomycin resistance at a genetic level. Microarray studies (unpublished) confirm a strong association between daptomycin resistance and perturbations in agr expression. Microarray studies provide important new insights in this regard. Jones T et al. Agents Chemo. 2007. For example, some aptomycin resistant mutants exhibit a substantial alteration in agr transcription. As daptomycin is a membrane-targeting lipopeptide, we compared a number of membrane parameters of initial blood isolates with subsequent daptomycin-resistant strains obtained in clinical treatment. In comparison to parental strains, resistant isolates demonstrated: i) enhanced membrane fluidity; ii) increased translocation of the positively-charged phospholipid, lyslyphosphotidyl-glycerol (LPG) to the outer membrane leaflet; iii) significantly increased net positive surface charge; iv) reduced susceptibility to daptomycin-induced depolarization; increased membrane permeabilization and reduced autolysis; v) significantly reduced surface binding of daptomycin; and vi) increased cross-resistance to cationic antimicrobial host defense peptides, hNP-1 and tPMP-1. These data correlate distinct changes in membrane structure and function with in vivo development of daptomycin resistance in MRSA. Moreover, they specify genetic determinants and regulatory events that may be critical to evolution of daptomycin-resistance phenotypes during treatment in humans, and how SAL may modulate adaptive responses of these MRSA resistome components. Given the clear impact of SAL on expression of agr and agr-dependent (e.g. hla) and sigB-regulated genes as noted above, it is entirely reasonable to pursue this line of investigation with agr, sar, and other key regulons as proposed the current project (see Research Plan).

SAL Exerts Putative Down-Regulatory Effects on the MRSA Virulon

Figure 4:
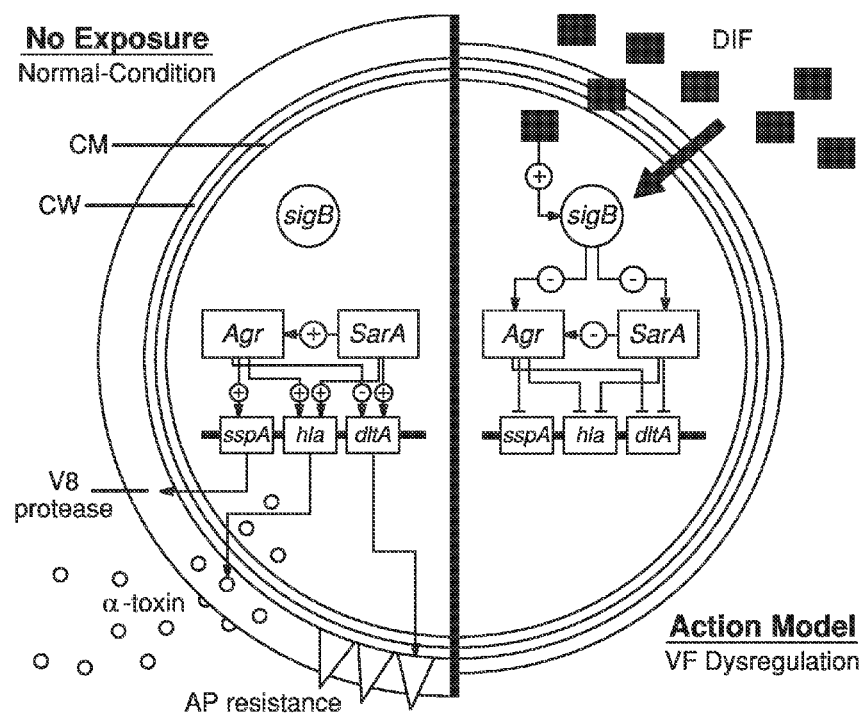
FIG. 4 shows a hypothesized model of SAL-mitigation of antibiotic resistance and virulence factor expression in MRSA in vitro, ex vivo, and in vivo. SAL exerts its anti-MRSA effects by modulating expression of adaptive genes and/or regulators thereof, such as sigB, agr, and sar.

The phenotypic and genotypic findings above provided a logical basis for our hypothesizing a network responsible for SAL-induced impacts on the staphylococcal virulon. Although sigB hyper-expression and sarA and agr-mediated down-regulation seem clear, the mechanistic basis for such effects is not understood. For example, sigB normally increases net sar operon expression. Karlsson and Arvidson, Infect Immun. 2002 70:4239-46. Thus, it is likely that sar P1 promoter occlusion related to sigB hyper-expression underlies seemingly paradoxical repression of sar expression in the presence of SAL. Kupferwasser et al. J Biol Chem. 2000 275:13863-71. Similarly, clfA, a key fibrinogen-binding adhesin gene, is normally induced by sigB. Goerke et al. Infect Immun. 2005 73:3415-21. SAL-mediated reduction in fibrinogen binding may relate to one of two phenomena: i) clfA promoter hindrance as above for sar; or ii) reduced expression of related fibrinogenbinding adhesins by SAL, including fnbA. Wann et al. J Biol Chem. 2000 275:13863-71. Based on these observations, a hypothetical model of the SAL-mitigated gene network is shown in FIG. 4. agr down-modulation is but one genetic readout of SAL-impacts, since sigB influences the S. aureus virulon and resistome as a whole. Thus, the collective impact of SAL in MRSA will afford a net enhancement of peptide antibiotic efficacy and reduced resistance. Shown herein is increased vancomycin efficacy by aspirin co-treatment in the IE model (FIG. 12) underscore this notion.

EXAMPLE IV

Adjunctive SAL can Improve Antibiotic Efficacy and Mitigate MRSA Resistance In vivo This example demonstrates that effects of SAL result in enhanced antibiotic prophylaxis, efficacy, and net outcomes in a rigorous in vivo model of S. aureus infection (IE) and confirm that adjunctive SAL can improve antibiotic efficacy and mitigate MRSA resistance.

Aspirin Improves Key Outcomes in Relevant Models of Infective Endocarditis (IE)

To begin to assess the in vitro data sets for in vivo relevance, the rabbit model of IE as described by Yeaman et al. Handbook of Animal Models of Infection. Academic Press, New York, N.Y., was utilized. Animals with pre-established IE caused by strain RN6390 were administered a wide range of iv aspirin dose regimens (4 to 12 mg/kg/d for 4d therapy). This range affords human-equivalent sera levels in rabbits as described in Kupferwasser et al. Circulation. 1999 99:2791-7. A consistent and dose-dependent reduction of vegetation weight, and vegetation and kidney bacterial densities resulted from aspirin treatment.

FIG. 11 shows aspirin (ASA) benefits outcomes in a rabbit model of S. aureus IE. Of special note is the finding that an 8 mg/kg/d dosage significantly exceeded beneficial effects of either the lower (4 mg/kg/d) or higher (12 mg/kg/d) dose regimens. This finding emphasizes the need to optimize PK-PD effects of SAL.

Figure 5:
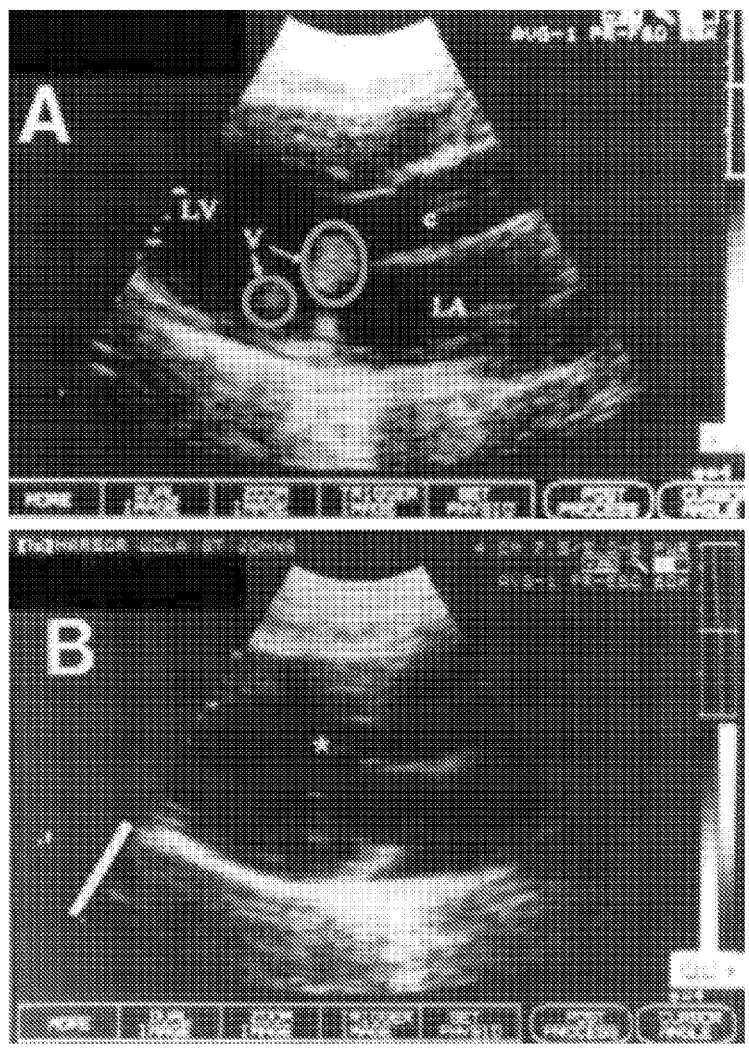
FIG. 5 shows that aspirin therapy mitigates MRSA Treatment (Log CFU/g±SD)

These remarkable findings were further amplified by dramatic reductions in mass of echocardiographic detectable cardiac valve vegations (FIG. 5; red circles). Of special note, there was a paradoxical loss of these beneficial effects as the aspirin dose increased to 12 mg/kg/d. Moreover, the same paradoxical finding, SAL impacts on plasma prostacyclin levels were examined. The 12 mg/kg aspirin dosing (but neither at 4 or 8 mg/kg) caused a prolonged suppression of prostacyclin generation. As prostacyclin is crucial to normal anti-thrombotic tone of vascular endothelium, one possible explanation for the effect may be a more thrombotic milieu due to high dose aspirin. We will define the precise PK-PD parameters of SAL that optimally modulate antibiotic resistance and/or virulence gene expression in MRSA, using complementary in vitro, ex vivio, and in vivo methods as described by Kupferwasser et al. Circulation. 1999 99:2791-7.

FIG. 5 shows that aspirin therapy mitigates MRSA Treatment (Log CFU/g±SD) Relapse (Log CFU/g±SD) Regimen Vegetations Kidneys Vegetation Kidney Control 8.4±0.9 7.8±1.6—vegetation mass. Note striking reductions in echocardiograpic-definable vegetations as seen in untreated controls (5A) by SAL therapy (5B). The echocardiographic data seen here parallel the microbiologic data shown in FIG. 12. Taken together, these findings show that ASA and SAL beneficially impact the efficacy of anti-MRSA therapy by mitigating adaptive gene expression in the organism.

Salicylates Enhance In vivo Efficacy of Vancomycin in Established *S. aureus* IE The impact of aspirin on vancomycin efficacy in established IE was assessed. Consistent with the in vitro and ex vivo observations described herein, the adjunctive combination of aspirin with vancomycin synergistically enhances reduction in vegetation weight and target tissue bacterial count in an aspirin dose-dependent manner. These data are summarized in FIG. 12.

Aspirin Efficacy In vivo is Strain-Independent, sigB-Dependent, and Mediated by SAL To rule out a strain-specific effect of aspirin, studies were performed with a range of *S. aureus* strains, including well-known MSSA (6850) and MRSA strains (COL). Equivalent salutary effects of aspirin treatment were confirmed for rsbU-dependent and rsbU-independent pathways of SAL-induced sigB activation in vivo, in strain RN6390 as well as its rsbU-repaired variant, SH1000. In contrast, the impact of aspirin was dampened in strains deleted of their entire sigB operon. The same in vivo efficacy study was carried out with SAL and found equivalent results to aspirin alone. As SAL has no anti-platelet aggregation properties, direct antimicrobial—not anti-thrombotic effects—confer beneficial effects of aspirin in this model.

Aspirin Mitigates sarA P1 Expression in the In vivo Model of IE

To investigate the potential relationship of microbiologic and macroscopic vegetation impacts of SAL with gene expression effects seen in vitro, the same IE model described above was employed. Aspirin suppressed sarA P1 expression within vegetations (FIG. 6), as detected using the in vivo GFP::promoter fusion assay and in situ immunofluorescence as described in Wann et al. J Biol Chem. 2000 275:13863-71. These results affirmed two critical aspects of our proposed studies: 1) a SAL-mediated direct modulation of a key *S. aureus* regulatory gene in vivo; and 2) ability to detect this modulation in MRSA from IE tissues in real-time ex vivo.

Figure 6:
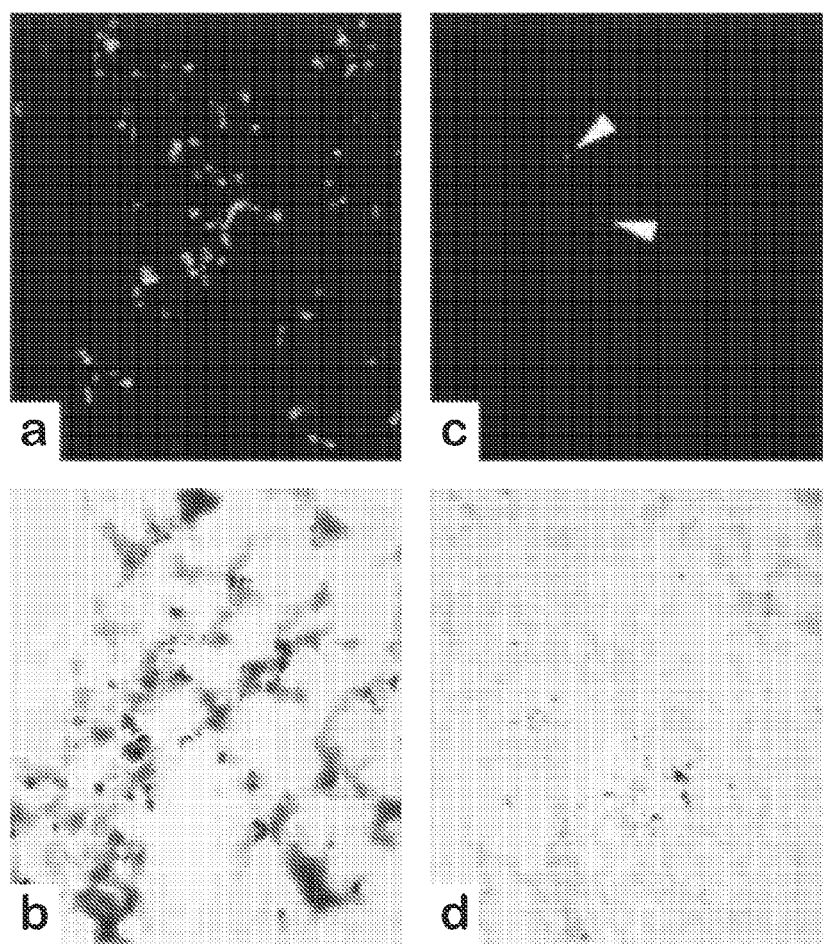
FIG. 6 shows that Aspirin suppresses sarA P1 expression in vivo.

FIG. 6 shows that Aspirin suppresses sarA P1 expression in vivo. Giemsa-staining and fluorescence analysis of P1:GFPuvr *S. aureus* constructs were performed on valve vegetations excised from rabbits with IE 24 hr following no treatment (control) or a single iv dose of 8 mg/kg aspirin. Panels 6A and 6B—respective fluorescence and Giemsa-stains in control animals; 6C and 6D—fluorescence or Giemsastains of aspirin-treated animals. Note marked reduction in *S. aureus* P1 signal and CFU due to aspirin.

The above described results demonstrate that aspirin (via SAL) impacts multiple phenotypic and genotypic features of *S. aureus* likely pivotal to endovascular pathogenesis. SAL mitigates key antibiotic resistance and/or virulence genes in MRSA, thereby rendering the organism less resistant to antibiotic killing, and less virulent. Our experiments described herein will rigorously determine the PK-PD optima of SAL for therapeutic efficacy and mitigation of resistance emergence.

EXAMPLE V

SAL Significantly Down-Modulates the Ability of MRSA Strains to Resist Peptide Antibiotics In vitro and In vivo This example demonstrates that SAL's beneficial effects derive from down-regulation of key antibiotic resistance and/or virulence genes, thus reducing overall virulence and rendering the organism more susceptible to killing. In turn, such gene modulation translates to dampening of resistance emergence.

SAL and/or its analogues will favorably impact vancomycin or daptomycin MPC and MSW. Such impacts can occur even if SAL-antibiotic combinations do not alter direct anti-staphylococcal efficacy of these agents (e.g. MIC, MBC, FIC, or FBC). Significant differences in the impacts of SAL or its analogues on the extent or kinetics of antibiotic resistance will distinguish mechanistic correlates of resistance. sarA, agr, and sigB regulatory gene expression is modulated by exposure to SAL and its analogues. MSCRAMM genes are subject to altered expression in the presence of SAL and/or its analogues. Similarly, SAL or analogues mitigate expression of virulence factor genes important to cardiovascular pathogenesis, including α-toxin (hla) and/or fnbA. The extent of target gene modulation differs substantially between SAL and its analogues. Accordingly, a structure-activity relationship will be defined among SAL analogues with: 1) exceptional down-regulation of key phenotypic or genotypic resistance determinants; or 2) desirable pharmacologic characteristics.

Computational modeling will identify consensus and/or unique SAL pharmacophores that optimally modulate antibiotic resistance or virulence gene expression, and assess whether such effects are governed by direct or indirect actions on regulatory genes as described by Yount, N.Y., and M.R. Yeaman. 2006. Biochem. Biophys. Acta 1758:1373-1386; Xiong et al. J Infect Dis. 2002 185:348-56; Xiong et al. Antimicrob Agents Chemother. 1999 43:1111-7.; Yeaman et al. Antimicrob Agents Chemother 2002; 46(12):3883-91; Yount et al. Antimicrob Agents Chemother 2004 48:4395-404; Yeaman et al. Biochim Biophys Acta. 2007 1768:609-19; Yeaman and Yount, Nature [Rev Micro] 5:727-40.; Yount and Yeaman, Proc Natl Acad Sci USA 2004 101(19):7363-8; Yeaman and Yount, ASM News 2005 71:21-7; Yeaman and Yount, Pharmacol Rev 2003 55(1):27-55; Yount and Yeaman, Protein Pept Lett 2005; 12(1):49-67; Yount et al. 2007 Biochem. Biophys. Acta. 1768:598-608; Yount et al. 2007. Biochem. Biophys. Acta. (In press).

This example is directed to quantitatively modeling the beneficial effects of SALs on efficacy of the current first-line peptide antibiotics for MRSA infections: vancomycin and daptomycin. Such modeling enables PK-PD characterization of resistance-mitigating and fficacy-enhancing effects of SALs to improve overall outcomes of antibiotic treatment of MRSA infection MRSA infection.

Figure 7:
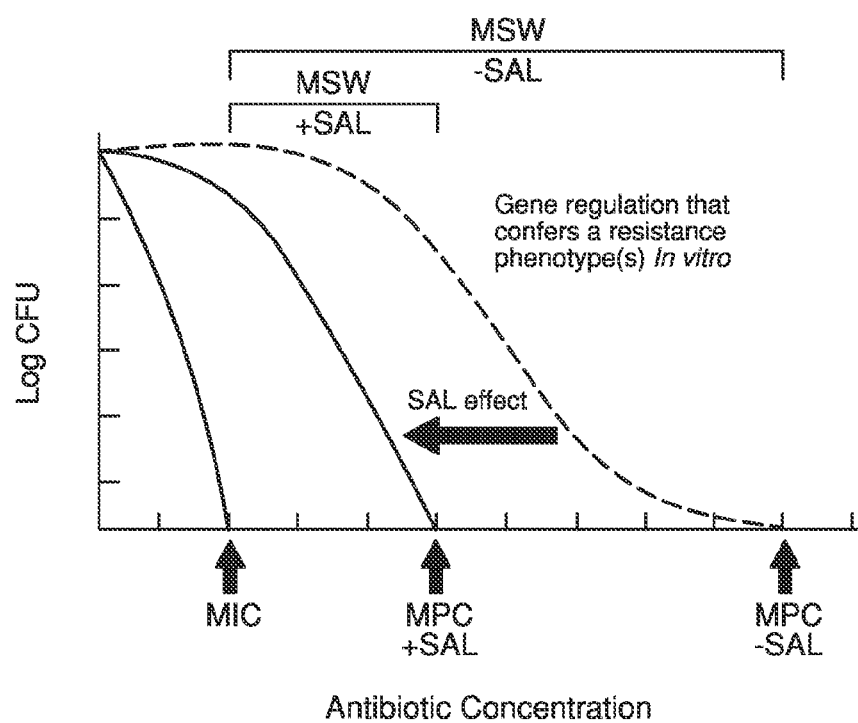
FIG. 7 shows a quantitative model for SAL mitigation of MRSA vancomycin and daptomycin resistance in vitro.

The experiments are designed to model the quantitative and kinetic influence(s) of SALs on phenotypic or genotypic events relevant to emergence or progression of MRSA resistance to vancomycin and daptomycin in vitro. First, innovative checkerboard assays will be used to define the kinetic impact of SAL on antibiotic fractional inhibitory concentration (FIC) and fractional bactericidal concentration (FBC)

over time and over successive growth generations. The influence of SAL on dynamics of antibiotic resistance will be further modeled using novel approaches to assess the effect of SAL on the antibiotic mutant prevention concentration (MPC) and the mutant selection window (MSW; detailed below). Results will then guide PK-PD studies in an ex vivo model of IE (Example VI), to evaluate antibiotic-SAL PK-PD relationships in complex human clinical settings simulating: 1) circulatory dynamics; and 2) tissue biomatrices. The results will generate a quantitative and qualitative model of the modulatory effects of SAL on antibiotic resistance in vitro, ex vivo, and in vivo. The following goals will be met:

A. Model quantitative relationships between SAL, vancomycin, or daptomycin that mitigate emergence of *S. aureus* phenotypic resistance to these two prototypic peptide antibiotics in vitro. For these studies, we will use a strategic panel of well-characterized and virulent MRSA strains reflecting both clinical and laboratory isolates, and including genome-sequenced strains. Integrated methods will assess impacts of SAL on antibiotic minimum inhibitory and bactericidal concentrations (FIC; FBC), mutation prevention concentration (MPC), and mutation selection window (MSW).

B. Model quantitative relationships between SAL, vancomycin, or daptomycin that mitigate emergence of *S. aureus* genotypic resistance to these two peptide antibiotics in vitro. Prototype genes to be assessed will prioritize putative loci involved in peptide antibiotic resistance, virulence, or regulation: [mprF, yycFG, vraRS]; [hla, fnbA, clfA, pvl]; and [agr, sarA, sigB], respectively. We will use realtime quantitative PCR as our primary expression probe; GFP-fusion beacons or lux-engineered strains will be used as needed to confirm gene expression profiles modulated by SAL.

C. Model SAL structural analogues for their potential to further enhance the modulation of phenotypic or genotypic *S. aureus* resistance to vancomycin or daptomycin in vitro. This component adds significant innovation to the project: 1) structure-activity modeling may reveal pharmacophores that mitigate *S. aureus* antibiotic resistance, and may be amenable to future investigation of therapeutic efficacy; and 2) consensus structures found to be capable of modifying *S. aureus* gene expression profiles will identify novel approaches to alter *S. aureus* resistance or virulence gene expression.

*S. aureus* Strain Panel.

A strategic panel of *S. aureus* strains will be studied (FIGS. 13 and 16). The panel will include representative, well-characterized and prototypic methicillin-resistant (MRSA) strains including, vancomycinsusceptible (VSSA) and vancomycin-intermediate susceptible (VISA) isolates, plus daptomycin-susceptible (DSSA) and daptomycin non-susceptible (DNSA) strain pairs from the same patient. Represented in this panel are clinical isolates and well-defined laboratory strains that have published genome sequences and have been used previously in animal model investigations. As the stress response regulon, sigma factor B (sigB), may have independent effect(s) on antibiotic resistance, all strains are sigB-positive. In contrast, the strain collection differs in agr genotypes, as agr type and function have been linked to: 1) distinct clinical syndromes; and 2) propensity for emergence of peptide antibiotic resistance. Although this strain panel is selected as the priority study set, our studies are designed to incorporate other critical strains available through NARSA (NIH/NIAID) or our collaborative network, should they become available or advantageous for study.

Organism Culture

*S. aureus* is cultured to logarithmic phase in Mueller-Hinton broth (Difco, Detroit, Mich.) plus Ca $Ca^{+2}$ (25 μg/ml [vancomycin] or 50 μg/ml [daptomycin]) and $Mg^{+2}$ (12.5 μg/ml) at 37° C. Bacteria are harvested by centrifugation, washed, counted by spectrophotometry, and resuspended in fresh MHB. Where indicated, tryptic soy agar (TSA; Difco, Detroit, Mich.) will be used for FIC or FBC evaluation. The VISA strain (MU-50) will be maintained on TSA containing vancomycin (4 μg/ml); all VISA, VSSA, DSSA, and DNSA status of strains will be validated prior to use by standard E-strip methods. For selected studies, organisms will be cultured to post-logarithmic phase to assess effects of SAL on resistance at distinct growth phases. Notably, the results and models are readily amenable to VRSA strains.

Antibiotics and SAL.

Pharmaceutical-grade vancomycin and SAL are obtained in powder form from Sigma (St. Louis, Mo.); daptomycin is obtained from commercial sources in powder form. Stock solutions of each antibiotic will be prepared in sterile 0.9% NaCl to achieve a concentration of 1 mg/ml, and stored at −70° C. until use. Dilutions will achieve desired target concentrations in each specific experiment.

Modeling the Impact of SAL on MIC, MBC, FIC and FBC Parameters of Vancomycin or Daptomycin Versus MRSA In vitro.

The influence of SAL on direct anti-staphylococcal efficacies of vancomycin and daptomycin in vitro versus the MRSA strain panel (FIG. 13) will be assessed. The impact of SAL on the antibiotic mutation prevention concentration (MPC) and mutation selection window (MSW) will be quantified. Results of these studies will establish quantitative relationships between SAL and vancomycin and/or daptomycin that enhance efficacy or mitigate phenotypic resistance versus MRSA. These investigations will show that two of the principle pathways of SAL-mediated resistance suppression are: 1) more rapid and extensive killing of the target organism; and 2) suppression of the evolution of antibiotic resistance in residual cell populations exposed to the agent-of-interest.

Quantitative Modeling of SAL on Antibiotic Efficacy and Resistance Versus MRSA In vitro.

A quantitative model of the influence of SAL on vancomycin or daptomycin MIC, MBC, FIC and FBC versus our strategic MRSA strain panel (FIG. 13) will be established. These parameters will be defined for antibiotics alone and in the presence of SAL by broth microdilution per Clinical Laboratory Standards Institute (CLSI) protocols. Results will be validated by E-test (AB Biodisk, Piscataway, N.J.) as detailed by Firsov et al. J Antimicrob Chemother 2006 58:1185-92; Clinical and Laboratory Standards Institute. Performance Standards or Antimicrobial Susceptibility Testing Sixteenth Edition: Approved Standard M100-S16. CLSI, Wayne, Pa., USA, 2006. SAL has no evident intrinsic bacteriostatic or bactericidal effects at physiologically relevant drug concentrations as will be used in these investigations as described by Palma et al. J Bacteriol. 2006 188:5896-903; Wann et al. *J Biol Chem.* 2000 275:13863-71; Kupferwasser et al. *Circulation.* 1999 99:2791-7. Therefore, the in vitro impact of SAL lone will only be included as a control in the proposed investigations in selected experiments.

As described below, complementary methods to quantify the impact of SAL on the emergence and progression of MRSA resistance to vancomycin and daptomycin in vitro will be employed. Results will provide a kinetic assessment of SAL on antibiotic efficacy and resistance at phenotypic and genotypic levels in MRSA MRSA:

A checkerboard technique will be employed to delineate MIC, MBC, FIC, and FBC of vancomycin or daptomycin+SAL combinations. Ninety-six well plates containing serial dilutions (range: 0.125 to 64 µg/ml) of antibiotic alone or with SAL (range: 0 to 50 µg/ml) are inoculated with 10 106 CFU/ml of S. aureus and incubated for 18 hr. This specific SAL concentration range was chosen to encompass clinically achievable serum levels with standard dosing regimens as described by Wann et al. J Biol Chem. 2000 275:13863-71; Kupferwasser et al. Circulation. 1999 99:2791-7. Control wells will be free of antibiotic or SAL. After incubation, plates are screened for visual growth (MIC). The FIC will then be calculated by standard methods. Wells will then be replica-plated onto TSA, and incubated to define MBC and to calculate the FBC. Next, the MPC and MSW of antibiotics alone and in combination with SAL will be defined by plating a centrifuge-conentrated $10^{11}$ CFU/ml inoculum from wells with highest concentrations of antibiotic in which growth is present into TSB media containing 2×-increased range of peptide antibiotic concentrations (i.e., 0.250 to 128 µg/ml). The $\log_{10}$ CFU/ml is then plotted vs. antibiotic concentration, and MPC defined at the intersection of the antibiotic concentration and limit of CFU detection (i.e. $\log_{10}$ CFU/ml=1.0; FIG. 7). Next, MSW is determined as the concentration span interposing the MIC and MPC. These data will provide three complementary and key endpoints: 1) efficacy of antibiotics alone (MIC, MBC) versus combined with SAL (FIC, FBC). Such outcomes will adjudicate the impact of SAL on the direct anti-staphylococcal efficacy of antibiotics; 2) MPC of antibiotics alone or in combination with SAL. These data will adjudicate the extent to which SAL modulates a threshold antibiotic concentration needed to suppress resistance; and 3) the MSW of antibiotic(s) alone or as combined with SAL. These data will further quantify an ability of SAL to constrict the MSW in which resistant mutants may first arise. These experiments will utilize a conventional static (single time end-point) mode. Adaptation of this method to model resistance emergence kinetically will be achieved. Detailed below, this approach will complement the above studies by defining how SALs modulate the temporal evolution of emergence and progression of resistance.

FIG. 7 shows a quantitative model for SAL mitigation of MRSA vancomycin and daptomycin resistance in vitro. Initial studies will determine the impact of SAL on direct antibiotic efficacy by defining FIC, FBC, MPC, and MSW in the strategic panel of MRSA isolates, as compared to antibiotics alone. SAL will mitigates emergence of resistance by modulating expression of antibiotic resistance effector(s) or regulatory genes. These effects would be reflected by a left-shift in the MPC and corresponding narrowing of the MSW, even if the MIC, FIC, and FBC are unaffected by SAL exposure. Such effect(s) are consistent with in vivo data, in which SAL combined with vancomycin yielded significantly greater efficacy versus invasive MRSA infection (IE) than did vancomycin alone.

Kinetic Modeling of SAL Mitigation of MRSA Antibiotic Resistance In vitro

Figure 8:
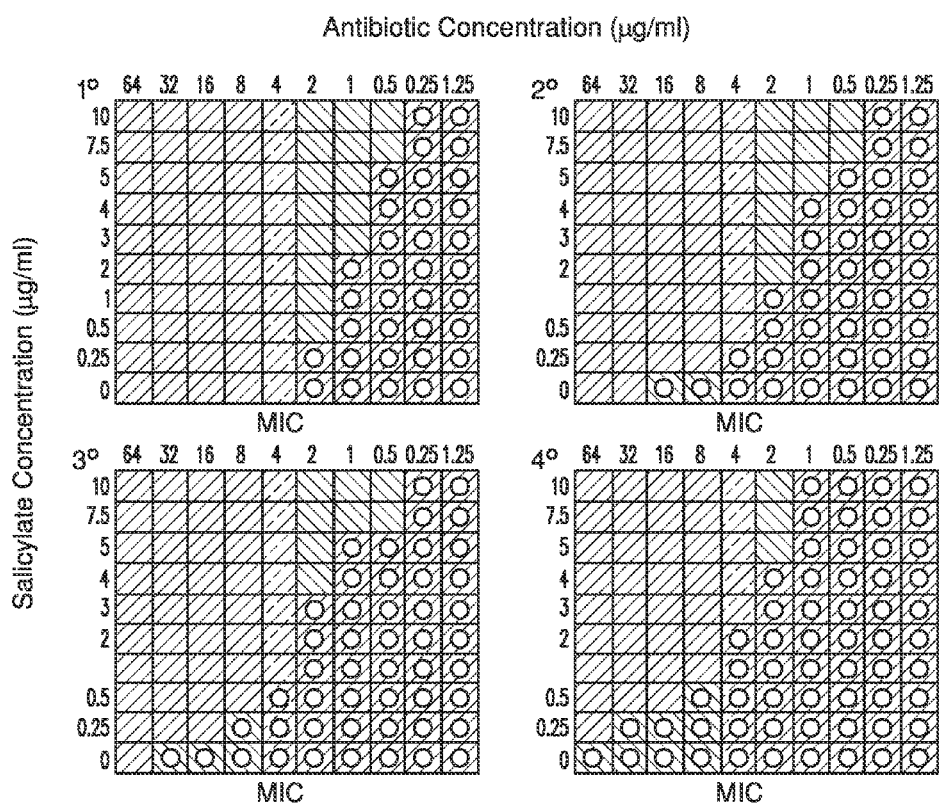
FIG. 8 shows kinetic in vitro modeling of SAL-mitigated MRSA resistance to vancomycin and daptomycin.

Kinetic profiles of SAL-mitigated vancomycin and daptomycin resistance to in vitro will be modeled. These studies will address two independent but related characteristics of resistance: 1) kinetics of the initial. emergence of resistance upon primary exposure to antibiotic (termed emergence kinetics); and 2) kinetics of ensuing progression of resistance over successive generations of drug exposure (progression kinetics). For these experiments, the checkerboard method described above was adapted to dynamically evaluate the temporal impact of SAL on MPC and MSW following initial exposure to antibiotics alone or in combination with SAL in vitro. This approach will enable tracking of two potential kinetic outcomes of SAL-antibiotic interactions: 1) emergence kinetics at 4, 8, 12, and 24 hr; and 2) progression kinetics over successive primary (1°), secondary) (2°, tertiary (3°), and quaternary (4°) generations (as depicted in FIG. 8, below). Results of these investigations will provide the temporal milestones of the influence(s) of SAL on emergence of antibiotic resistance following individual drug exposure, and in clones surviving successive exposures. The complementary approaches will confirm that SAL synergistically enhances antibiotic efficacy (i.e., a reduced level and/or an expedited time to reduced antibiotic MIC or MBC—green area in FIG. 8, below), and/or suppresses emergence and progression of antibiotic resistance (i.e., dampened or delayed increase in MIC or MBC—red area in FIG. 8, below). The results will also further elucidate antibiotic efficacy contributions to therapeutic outcomes.

FIG. 8 shows kinetic in vitro modeling of SAL-mitigated MRSA resistance to vancomycin and daptomycin. The figure depicts two distinct but potentially related anticipated outcomes: 1) enhanced efficacy of antibiotics combined with SAL (green area); and 2) mitigation of emergence of resistance due to SAL (red area). The impact of SAL on such resistance phenotypes will be modeled over an initial exposure period (emergence kinetics), as well as across successive generations (progression kinetics). Experiments are designed to model relevant dynamics during antibiotic resistance as occur in therapeutic success versus failure. A beneficial impact of SAL on efficacy and resistance over time not only upon initial exposure, but also over primary (1°) to quaternary (4°) generations. By using strategic MRSA strains tha in specific regulatory or effector genes, outcomes will also reveal insights into potential coordinate control of antibiotic resistance genes.

Emergence Kinetics.

A key event in the development of resistance is the. initial emergence of the resistance phenotype on antibiotic exposure. This event is distinct from resistance dissemination to progeny (vertical transmission) or bystander organisms (horizontal transmission). Hence, as part of the kinetic modeling studies above, replica samples will be plated onto three TSA conditions at 4, 8, 12, and 24 hr times: 1) TSA alone; 2) TSA+antibiotic at its respective MIC for the organism-of-interest (antibiotic MIC MIC); and 3) TSA+antibiotic MIC+SAL. In the latter case, concentration ranges of SAL will be guided by results from FIC and FBC assays above shown to most favorably impact antibiotic efficacy and/or suppress resistance. These results will chronologically assess the impact of SAL on emergence of antibiotic resistance in strains upon their initial exposure to vancomycin or daptomycin.

Progression Kinetics.

The potential mitigating activities of SAL on progression of resistance phenotypes over successive generations of MRSA in vitro (FIG. 8) will be evaluated. In these studies, organisms from wells at the intersection of lowest antibiotic MIC with and without SAL will be subjected to consecutive modeling as above over the course of 4 consecutive rounds of antibiotic exposure. Results will provide the kinetic profiles of the impact of SAL-mitigation of antibiotic resistance progression to progeny in successive MRSA generations. The findings will also facilitate the computational modeling of the impact of SAL on AUC:MIC ratios to optimize efficacy and suppression of resistance vs. MRSA ex vivo and in vivo (Specific Aims 2 and 3). This ratio is potentially correlated with vancomycin efficacy, where an AUC:MIC ratio of ≥400:1 has been associated with improved outcomes as described by Sakoulas et al. Antimicrob Agents Chemother. 2006 50:1581-5; 111 Saskoulas G et al. J Infect Dis 2003 187:929-38; Saskoulas et al. Clin Infect Dis 2006 42:540-50.

In vitro Timed-Kill Studies

Key outcomes from the kinetic studies above will be validated using established timed-kill methods. Three vancomycin and daptomycin concentrations will be selected for time-kill studies based on: 1) MIC; 2) MSW midpoint; and 3) MPC (FIG. 7). The SAL concentrations to be used will encompass those found to be synergistic in vitro as above. High inocula ($10^8$ CFU/ml) will be used to favor detection of resistance emergence, and SAL mitigation thereof. At each time point (0, 1, 2, 4, 8 and 24 hr), a 20 μl aliquot will be plated in triplicate onto TSA alone or TSA containing antibiotic at concentrations of 3× and 6× the vancomycin or daptomycin MIC to detect clinically-relevant resistant clones. Appropriate washing and dilution steps will be performed to minimize antibiotic carryover, and plates incubated at 37° C. for 24 hr (antibiotic-free TSA) or 48 hr (antibiotic-containing TSA). The log C $\log_{in}$ CFU/ml is then plotted versus time to produce kill curves. All experiments will be carried out in duplicate. Outcomes of these studies will validate quantitative antibiotic-SAL relationships that beneficially modify antibiotic efficacy and/or mitigate resistance.

Modeling Quantitative Relationships Between SAL, Vancomycin, or Daptomycin that Mitigate MRSA Genotypic Resistance to these Prototypic Antibiotics In vitro Direct relationships exist between SAL exposure and *S. aureus* gene expression that are extremely relevant to therapeutic efficacy. The impact of SAL-antibiotic regimens will be evaluated on three classes of genetic determinants that have putative association with vancomycin or daptomycin efficacy or resistance (FIG. 14): 1) regulatory genes implicated in governing resistance adaptation: agr, sarA, and sigB; 2) representative effector genes that are believed to mediate resistance to peptide antibiotics: vraRS, mprF; and yycFG; and 3) structural genes involved in staphylococcal virulence (e.g., surface adhesins fnbA, clfA and secreted toxins such as hla and pvl; see FIG. 14, below).

Selection of Target Genes of Interest for Assessment of SAL-Modulated Expression Regulatory Genes and Networks.

Expression of *S. aureus* virulence gene repertoires is governed by a complex and multifactorial regulatory and counter-regulatory gene networks. Two principal examples of such loci in *S. aureus* are the staphylococcal accessory A regulon (sarA), and the accessory gene regulon (agr). In turn, these regulons are subordinate to broader stress-response pathways, including those controlled by sigB (see FIG. 4). As shown herein, SAL modifies the expression of such regulatory genes in vitro and in vivo; these impacts are principally linked to sigB expression as described by Palma et al. J Bacteriol. 2006 188:5896-903; Wann et al. J Biol Chem. 2000 275:13863-71; Kupferwasser et al. Circulation. 1999 99:2791-7. Potential modulatory impacts of SAL antibiotic combinations on these regulons will be evaluated.

Antibiotic Resistance Effector Genes.

The "resistome" of MRSA for vancomycin or daptomycin includes several specific effector genes that likely mediate direct countermeasures to principal mechanisms-of-action of these antibiotics. For example, altered sequences (mutation) or altered expression of the genes mprF, yycFG, and rpoB/C correlate with changes in the envelope characteristics of MRSA that appear to be responsible for conferring daptomycin resistance as described by Friedman et al. Antimicrob Agents Chemother. 2006 50:2137-45. Similarly, abnormal expression profiles of the two-component regulatory system, vraRS, has been correlated to increased resistance to peptide antibiotics as described by Gardete et al. Antimicrob Agents Chemother. 2006 50:3424-34. Thus, the influences of AL-antibiotic combinations on expression of such putative peptide-resistance genes will be demonstrated.

Virulence Factors.

Along with direct effects on expression profiles of the above genes, as demonstrated above, SAL modifies key virulence factor expression in vitro and in vivo. Such down-modulation of virulence likely allows more efficient antibiotic-mediated bacterial clearance. In turn, this effect indirectly reduces propensities for organisms to emerge as resistant in the face of antibiotic exposure.

Microbial Surface Components Recognizing Adhesive Matrix Molecules (MSCRAMMs): Most MRSA strains express multiple surface adhesins (over 20) that enable the pathogen to adhere to a wide variety of host substrates, a number of which are important in endovascular pathogenesis as described by Patti et al. Annu Rev Microbiol. 1994 48:585-617, Rivas et al. Curr Opin Drug Discov Devel. 2004 7:223-7. Many MSCRAMM genes are present in virtually all *S. aureus* strains (e.g., fnbA), while others are more variably expressed, and tend to be over-represented in patient-specific populations (e.g., collagen-binding adhesin [cna] in patients with bone and joint infections as described by Patti et al. Annu Rev Microbiol. 1994 48:585-617, Rivas et al. Curr Opin Drug Discov Devel. 2004 7:223-7 Our preliminary data indicate that MRSA strains associated with persistent bacteremia despite vancomycin therapy bind fibrinogen and fibronectin better than strains linked to resolving bacteremia.[118,124] Therefore, we will examine the influence of SAL-antibiotic combinations on the expression of prototype MSCRAMM genes involved in such ligand binding (fnbA; and clfA).

Staphylococcal Toxins: In relevant contexts of high bacterial density or entry into stationary growth (e.g. intravegetation colonies; abscesses), *S. aureus* undergoes a phenotypic shift from an adhesive-dominant ("colonization") phenotype, to a toxin-dominant ("invasive") phenotype. This phenotypic transition is regulated at the genetic level by, among others, sarA and agr regulons. In our preliminary studies, we screened 12 representative toxin genes correlating to clinical MRSA syndromes, including toxic shock syndrome toxin-1 (tsst-1) and 11 enterotoxin genes (sea-to-seo). Possession of tsst-1 was significantly overrepresented among persisting vs. resolving MRSA bacteremia isolates (86% and 44%, respectively; P=0.03). In contrast, no differences in distribution of enterotoxin genes were observed in the two cohorts. The hla gene encoding α-hemolysin (*S. aureus* α-toxin) is an important virulence factor in context of endovascular infection as described by Greene et al. Mol Microbiol. 1995 17:1143-52; Patti et al. Annu Rev Microbiol. 1994 48:585-617. In contrast, Panton-Valentine leukocidin (encoded by gene, pvl) among community-acquired MRSA strains has thus far been viewed as either a bona fide virulence factor primarily in necrotizing pneumonia, or a surrogate marker for other genotypic or phenotypic parameters of hyper-virulence as described by Voyich et al. J Infect Dis. 2006 194:1761-70; Labandeira-Rey et al. Science. 2007 315:1130-3. A positive trend associating pvl in persistent bacteremia strains (76% pvl-positive) versus resolving strains (56% positive) has been shown herein. Therefore, the effects of SAL-antibiotic combinations on hla and pvl expression will be confirmed.

The target genes were prioritized based upon: 1) modulatory effects of SAL on several of these genes; 2) in vivo data implicating a direct relationship between the selected gene expression and persistent MRSA bacteremia, despite vancomycin therapy; and 3) published literature verifying the in vitro impact of these genes on peptide antibiotic action or resistance. While the selected genes are particularly relevant to endovascular infections; distinct gene cadres can be more relevant to skin and soft tissue or pulmonary infections.

In these experiments, quantitative real-time PCR (qRT-PCR) will assess the differential expression of target genes in response to antibiotic alone, SAL alone, or SAL-antibiotic combinations. Drug concentration regimens to be used will be those as guided by results from the in vitro indices identified above reflecting effective ranges that: 1) enhance vancomycin or daptomycin efficacy; and/or 2) suppress emergence of drug resistance. Therefore, the study strains will be grown to log phase in the above concentration ranges of vancomycin or daptomycin in the presence of absence of SAL.

Multiplex qRT-PCR (mPCR) will be performed using protocols that have been thoroughly established in our own and collaborators' laboratories as described by Friedman et al. Antimicrob Agents Chemother. 2006 50:2137-45; Zhao and Drlica, J Infect Dis. 2002; 185:561-5; Chan et al. J Am Coll Cardiol. 2003 42:775-80; Fowler et al. 2007. J. Infect. Dis. 196:738-47. Briefly, proposed mPCR studies are designed to simultaneously evaluate bundles of 5 candidate genes, plus a positive control (poll) in each assay. Genomic *S. aureus* DNA is extracted using the Wizard Genomic DNA purification kit (Promega), modified such that 30 μg lysostaphin/ml are included in the lysis step. Primers and conditions are established as defined elsewhere by Feil et al. J Bacteriol 185: 3307-3316; Spratt, B. G. 1999 Curr Opin Microbiol 2:312-316; Feil and Spratt, B.G. 2001 Annu Rev Microbiol 55:561-590; Enright et al. 2000. J Clin Microbiol 38:1008-1015; Koreen et al. 2004. J Clin Microbiol 42:792-799; Oliveira and de Lencastre, 2002 Antimicrob Agents Chemother 46:2155-2161.

For each target gene selected, four or more sequences from different *S. aureus* strains (if available) will be analyzed by the Vector NTI alignX program. Sequences are aligned and primers from conserved regions of the gene chosen; priority will be given to anticipated mPCR fragments expected to be 300-800 bp, with a melting temperature of 60° C. In most cases, primers for target genes have been published, and will be prioritized. Any negative results for target genes will subsequently be validated using uniplex PCR. As may be necessary, depending on the results emanating from this study, strategic promoter/gfp reporter fusions will be constructed to confirm modulatory effects of antibiotic-SAL combinations upon specific target gene expression as described by Xiong et al. J Infect Dis. 2002 186:668-77; Xiong et al. J Infect Dis. 2006 194:1267-75; Xiong et al. Infect Immun 2004 72:1832-6. Statistical analyses will be conducted as detailed at the end of the Research Plan.

Modeling SAL Structural Analogues for Comparative Mitigation of Phenotypic or Genotypic Vancomycin or Daptomycin Resistance In vitro.

The results shown herein support the methods of prevention and treatment of life-threatening *S. aureus* infections. Chemically-defined SAL analogues that exceed SAL in beneficial effects on in vitro phenotypic resistance (e.g., reduced MPC), and modulation of MRSA target gene expression profiles will be provided by the invention. Structure activity relationship modeling will be used to reveal consensus or unique pharamacophores that modulate MRSA target genes-of-interest and new targets for anti-resistance strategies to improve efficacy of anti-MRSA antibiotics will be provided.

As shown herein, SAL administration significantly enhances antibiotic efficacy in *S. aureus* infections in vivo by modulating expression of key genes involved in antibiotic resistance and/or virulence. However, among the broader family of non-steroidal antiinflammatory agents (NSAIDs), neither aspirin (parent compound of SAL) nor indomethacin caused detectable changes in phenotypic or genotypic characteristics of three distinct *S. aureus* strains in vitro. Hence, a relative specificity exists regarding SAL as compared with other clinical NSAIDs as regards phenotypic and genotypic aspects of resistance that will be examined in this project. Moreover, these data substantiate the requirement for the conversion of acetylsalicylic acid (aspirin) to SAL to achieve full disclosure of the beneficial antimicrobial properties effects of aspirin in vitro and in vivo. These findings also substantiate the concept that the anti-infective properties of aspirin likely occur by both platelet-dependent (aspirin) and plateletindependent (SAL) mechanisms. Thus, the discovery of adjunctive use of SALs for MRSA infections are particularly relevant given: 1) long-term and extensive experience of aspirin for a variety of clinical indications; 2) its well-defined pharmacokinetics; and 3) its excellent adverse event and safety profiles. For these reasons, representatives of two major classes of SAL analogues will be investigated to confirm their ability to mitigate phenotypic and/or genotypic resistance and enhance the efficacy of vancomycin and daptomycin against MRSA:

Natural 2° metabolites—aspirin is converted to two primary metabolites in humans. Following initial de-acetylation (yielding SAL), SAL is converted to salicyluric acid by conjugation to glycine. In a parallel pathway, SAL is converted to gentisic acid as a result of mixed function oxidases. Whether either or both of these metabolites modulate MRSA resistance phenotype or genotype is unknown. Both compounds are commercially available (e.g. Sigma) for our testing.

Synthetic SAL analogues—the ability of synthetic SAL analogues containing strategic nuclear substitutions for modulation of MRSA phenotypic and/or genotypic resistance will be investigated. Flufenisal is a SAL analogue containing a fluorophenyl ring conjugation; importantly, like SAL, its bioactive form in vivo is deacetylated. Similarly, diflunisal is a SAL analogue modified to contain a di-fluorophenyl ring. Biochemical and clinical study data show these analogues to be 2-3 fold more active than aspirin in terms of cyclooxygenase functions. De Vroey P. Curr Med Res Opin. 1978 5:544-7. Importantly, both agents have undergone clinical testing for human therapy as NSAIDs. It is also noteworthy that SAL-phenyls and bi-phenyls share potential pharmacophores with auto-inducing peptides of quorum-sensing in MRSA. Lyon, G. J., and Novick, R. P. 2004. Peptides 25:1389-1403. Ji, G., Beavis, R., and Novick, R. P. 1997. Science 276:2027-2030. These relationships are pertinent to our hypothesis that SAL and its structural analogues mitigate antibiotic resistance or virulence via their modulatory effects on specific signal-mediated ene regulation in MRSA. Each the above analogs are commercially available for study.

Assessment of SAL Analogues on MRSA Phenotypic Resistance to Vancomycin and Daptomycin In vitro vitro.

Salicyluric acid, gentisic acid, flufenisal, and diflunisal will be tested for their ability to modify vancomycin or daptomycin efficacy against MRSA, and modulate phenotypic resistance in vitro as described above. SAL will be included as a control molecule in all experiments for comparison. Concentrations of salicyluric acid and gentisic acid will be guided by those of SAL above in our in vitro assays. Based on published data of their greater potency, the concentration range of flufenisal and diflufenisal to be examined will encompass a 2-fold lesser range than that for SAL, and mirror levels seen in clinical settings. Outcomes will be compared to SAL: 1)

enhancement of antibiotic efficacy (e.g. reduced MIC, MBC, FIC, or FBC); and 2) suppressed extent or kinetics of resistance emergence (e.g. left-shifted MPC or narrowed MSW). A minimal metric for defining a significant improvement in the impact of SAL analogues as compared to SAL itself will be an equivalent or greater phenotypic effect observed at a 2-fold or lower concentration of the analogue.

Assessment of SAL Analogues on MRSA Genotypic Resistance to Vancomycin and Daptomycin In vitro vitro.

The SAL analogues will also be assessed for their ability to modulate vancomycin or daptomycin genotypic resistance in vitro. In these studies, we will follow methods outlined in Specific Aim section 1B, above. As before, SAL will be included as a control in each experiment, and the concentration ranges of flufenisal and diflufenisal will span 2-fold lower than SAL. Differences in critical outcomes will be quantitatively and qualitatively compared to SAL: 1) modification of regulatory loci (sarA, agr, sigB), putative antibiotic-resistance effector loci (mprF, yycF/G, vraSR), and virulence factor loci (hla, fnbA, clfA, pvl) gene expression profiles; or 2) suppression of extent or kinetics of resistance genotypes. As above, we will define a significant increase in efficacy of the genetic impact of SAL analogues versus SAL as an equivalent or greater odulation of expression profile observed at 2-fold or lower analogue concentration.

As shown herein, SALs can significantly modify MRSA phenotypic and genotypic resistance to vancomycin and daptomycin, yielding enhanced antibiotic efficacy and suppressed virulence factor expression in vitro and in vivo Importantly, these effects translate to substantially greater antibiotic efficacy versus invasive *S. aureus* infection in vivo than antibiotics alone. The pharmacologic modulation in expression of the MRSA resistome and virulon by SALs enables anti-staphylococcal strategies disclosed and claimed herein. Thus, this application provides therapeutic modalities for improved prevention or treatment of life-threatening MRSA infections.

EXAMPLE VII

Modeling SAL-Mitigated Phenotypic and Genotypic Antibiotic Resistance of MRSA in Distinct Tissue Contexts Ex vivo This example demonstrates that SAL and analogues modulate antibiotic resistance and efficacy in distinct ways in circulating organisms versus those embedded deep within tissues. The organisms differ in expression profiles that are associated with regulation of genes that govern resistance to antibiotics or virulence, and that can be modulated by SALs.

The experiments will yield a comparative quantitative and qualitative assessment of the impact of SAL on antibiotic efficacy and resistance in relevant distinct contexts of infection. Moreover, they will reveal the impact of SAL on expression of regulatory, antibiotic-resistance, and virulence genes-of-interest among circulating versus SEV-phase organisms. Statistical analyses will be conducted with a model that prioritizes drug concentrations and PD parameters as determined in the preceding examples to enhance efficacy or suppress resistance emergence. Organisms from distinct fluid vs. tissue contexts of the model will exhibit non-identical phenotypic and genotypic relationships with regard to combined SAL-antibiotic responses. SAL will augment antimicrobial efficacy or suppress resistance in circulating organisms more significantly than organisms embedded in the established SEV matrix. *S. aureus* cells have more active expression of genes associated with antibiotic resistance, virulence, or regulation, will be more subject to SAL-mediated mitigation. This discovery is consistent with the observation that relatively senescent organisms deep within target tissues or biofilms often exhibit a considerably different repertoire of gene expression than planktonic cells as described by Proctor et al. Nature [Rev Micro]. 2006 (4):295-305. Moreover, organisms embedded within tissues may well be exposed to lower SAL or peptide antibiotic exposure concentrations than circulating cells related to penetration kinetics. Any significant SAL-mediated enhancement of antibiotic efficacy or reduction in resistance in MRSA within infected vegetations as discovered and described herein could represent a major breakthrough in treating invasive infections that are refractory to conventional therapies therapies.

The effect(s) of SAL on phenotypic and genotypic resistance of *S. aureus* in complex biomatrices simulating fluid and tissue phases of endovascular infection is shown herein. The quantitative correlates of SAL and analogue(s) on vancomycin and daptomycin efficacy and resistance is demonstrated in a pharmacologic model that simulates human PK-PD. This approach provides a detailed understanding of relevant impact of SAL-mitigated antibiotic resistance in biomatrices of infection ex vivo.

The kinetic interrelationships of SAL, vancomycin, or daptomycin on the phenotypic resistance profiles of *S. aureus* will be demonstrated in a controlled system simulating dynamic peak versus trough concentrations and AUC:MIC ratios of antibiotic and SAL. Studies will prioritize PK parameters disclosed herein and identified as mitigating MRSA resistance to vancomycin or daptomycin, or enhancing antistaphylococcal efficacy thereof.

To discern the mitigating effects of adjunctive SAL combined with vancomycin or daptomycin on relevant genotypic resistance profiles of *S. aureus* when residing in distinct tissue contexts of this model system, including circulating organisms versus those embedded within infected vegetations.

Overview of the Ex vivo Model of MRSA Infective Endocarditis Endocarditis.

An ex vivo model of human IE (FIG. 9) has been described by Mercier et al. Antimicrob Agents Chemother. 2004 48:2551-7; Mercier et al. Infect Immun. 2000 68:4699-705; Kang and Rybak, 1995 Antimicrob. Agents Chemother. 39:1505-1511; Rybak et al, 1997 Antimicrob. Agents Chemother. 41:1359-1363. The original model described by Rybak et al, 1997 Antimicrob. Agents Chemother. 41:1359-1363 (initially designed to evaluate antibiotic efficacy) was modified to study anti-infective agents in relevant and complex biomatrices, including both the surfaces and interiors of platelet-fibrin clots and used to show that platelets function in defense against *S. aureus* infection. Mercier et al. Antimicrob Agents Chemother. 2004 48:2551-7; Mercier et al. Infect Immun. 2000 68:4699-705. The model has consistently validated its equivalence to experimental IE with regard to antimicrobial PK-PD, and infection outcomes. Importantly, this model represents two distinct contexts of infection: 1) fluid phase phase, simulating bloodstream circulation. Here, media (SMHB) reservoirs were connected to the model chamber to allow entry and exit of fresh and exhausted media, respectively. The fluid component of the model is under continuous flow to simulate hematogenous movement; and 2), tissue phase phase, platelet-fibrin clots suspended in the circulating media to simulate infected tissue contexts. The *S. aureus* strains chosen for these ex vivo studies will be the same as utilized above, irrespective of whether or not they exhibit phenotypic or genotypic mitigation of antibiotic resistance or efficacy in the presence of SAL-antibiotic combinations in vitro. Use of this model enables confirmation that SAL differentially mitigates MRSA resistance and virulence in distinct contexts of infection.

Figure 9:
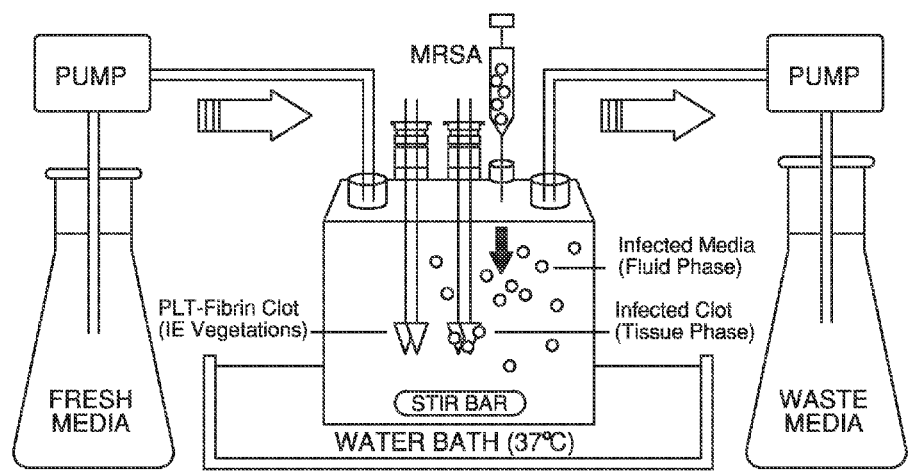
FIG. 9 shows xx vivo PD model of MRSA invasive infection used in the Examples.

FIG. 9 shows an ex vivo PD model of MRSA invasive infection used in the Examples. Experiments will use this validated model to confirm that SAL or analogues thereof exert related but non-identical effects on vancomycin or daptomycin efficacy and resistance by MRSA in circulating vs. tissue contexts of infection. The model controls kinetic rates of antibiotic and SAL to mirror half-lives, and simulates both tissue (IE vegetations) as well as circulating bloodstream environments, where MRSA likely differs in response to antibiotics.

Preparation of Simulated Colonized Vegetations. The simulated endocardial vegetations will be prepared as previously described by combining 0.9 ml of human platelet cryoprecipitate reagent (United Blood Services), 0.05 ml of aprotinin solution, and 0.05 ml washed platelet-rich plasma $10^8$ platelets/ml diluted in 0.9% NaCl. To infect the vegetations, 0.1 ml of washed organisms are introduced to achieve final inocula of $10^3$, $10^6$, or $10^9$ CFU/g. This inoculum range encompasses MRSA densities observed in early, progressive, and mature endocarditis lesions, respectively, in experimental animals and humans. Wann et al. J Biol Chem. 2000 275: 13863-71; Kupferwasser et al. Circulation. 1999 99:2791-7. A sterile monofilament line is inserted and 0.1 ml of bovine thrombin (5000 U in 5 ml sterile CaCl CaCl2[50 mmol]) are added to catalyze clotting. Resulting infected vegetations typically contain 250,000-300,000 platelets/g in a matrix mirroring that of human cardiac vegetations. Next, simulated vegetations are suspended from four sampling ports (two clots per port) in the model. Importantly, antibiotics and SAL or analogues can be introduced preceding, concurrent with, or following inoculation. The entire model is then placed in a water bath to maintain 37° C.

Modeling the Effective Pharmacodynamics (PD) of Antibiotic-SAL Relationships.

Dynamic concentrations of antibiotics, SAL and/or analogues thereof will be assessed to provide a quantitative basis for evaluating observed effects on antibiotic resistance or efficacy. Vancomycin concentrations will be determined by fluorescence polarization immunoassay (Abbott Diagnostics, TDx). Concentrations of daptomycin will be determined by bioassay utilizing *Micrococcus luteus* ATCC 9341. SAL and analogue concentrations will be assessed using a standard colorimetric assay. Half-life, AUC/MIC ratio, and peak concentration of agents will be calculated using a linear trapezoidal method implemented with PK Analyst software (MicroMath Scientific Software, Salt Lake City, Utah). One-compartment infection models (250 ml) will be performed in duplicate, with two simulated vegetations to be used in the models for each PD time-point. Each model will use continuous supplementation of fresh SMHB from sterile reservoirs (simulating vascular fluid phase compartment). A peristaltic pump will supply and remove the media from the model at a half-life equal to 6 h for vancomycin and 9 h for daptomycin. At this rate, the egress of *S. aureus* from the model is negligible since the doubling time (~20 min) far exceeds the loss attributed to media exhaust. Mercier et al. Infect Immun 2000 68:4699-705; Rybak et al, 1997 Antimicrob. Agents Chemother. 41:1359-1363. A magnetic stir bar will constantly circulate the central compartment media. Experiments will be conducted over 72 h. Dynamic time-points will be taken throughout the experiment (T=0, 8, 24, 32, 48, 56, and 72 h). At times 0, 1, 2, 4, 8 and 24 h, vegetation and fluid samples will be removed and processed as detailed below. These time points specifically minor early induction, ensuing proliferation, and hematogenous seeding phases of IE. Mercier et al. Antimicrob Agents Chemother. 2004 48:2551-7; Mercier et al. Infect Immun 2000 68:4699-705.

At each time-point, two simulated endocardial vegetations (SEVs) will be removed from each model (total, four SEVs per time-point; FIG. 1), weighed and processed by homogenization for quantitative culture. Serial dilutions of homogenized SEVs will be plated in triplicate onto tryptic soy agar (TSA; Difco, Detroit, Mich.), incubated for 24 h at 37° C. and the colonies counted. All samples will also be plated onto TSA containing vancomycin or daptomycin at 3× and 6× the MIC of each isolate to detect the presence of resistant mutants. Daily MICs will also be assayed via E-test for isolates sampled from the models. Means of the four samples at each time point will be plotted on time-kill curves as log C log 10 10 CFU/g versus time. Two samples from the MEM media of the central compartment of each model will also be taken at the same time-points and will represent bloodstream organisms. Means of samples from the two models will be plotted as log log 10 10 CFU/ml vs. time. For antibiotic treatment, vancomycin will be introduced to simulate clinically recommended doses in patients with normal renal function and for susceptible strains with MICs of ≤1 ug/ml (1 gram IV every 12 h); this is equivalent to a peak level of 35-40 µg/ml, and a trough level of approximately 10-15 µg/mL. Vancomycin will also be tested to simulate fAUC/MIC previously associated with the development of resistance (fAUC/MIC of 14, 28 and 56) in a similar model. 170 Daptomycin regimens will be dosed to achieve fAUC/MIC ratios of 16, 32, and 64 which have previously been correlated with induction of resistance in *S. aureus*. Finally, based on efficacy and resistance mitigation results from Aim 1, vancomycin and daptomycin will be introduced so as to represent model-predicted efficacious initial concentrations in this system. Kinetic samples will be taken from the central compartment of the models to monitor dynamic concentrations of antibiotics alone or in combination with SAL or analogues. Samples taken at 0, 0.5, 1, 2, 4, 8, 12, 24, 32, 48, 56 and 72 hr will encompass multiple half-lives for both vancomycin (6 hours) and daptomycin (9 hours), and will be flash frozen and stored at −70° C. for assays to quantify respective concentrations over the studied period. These data will enable us to model the kinetic peak and trough trajectories of antibiotics, SAL and/or analogues alone and in combination. Moreover, these data will be temporally compared to outcomes of antibiotic efficacy, phenotypic resistance, and genotypic resistance profiles. Growth controls will be performed for each bacterial strain under conditions that simulate both the 6 and 9 hours half-lives. To ensure physiologic testing conditions within the central compartment of the model, pH will be assessed and adjusted as required at several time-points during each experiment. These studies will provide the foundation for the combined SAL-antibiotic studies below.

Modeling the Impact of SALs on Anti-*S. aureus* Efficacy of Antibiotics in Distinct Contexts of Infection. The effect of SAL or selected analogue(s) on MRSA bacterial densities within SEVs will be determined. In these studies, SAL or analogues thereof found in to have efficacy will be evaluated alone or as combined with vancomycin or daptomycin ex vivo for anti-staphylococcal phenotypic impacts. Models will be performed as detailed above, where SMHB will contain vancomycin or daptomycin at MIC or MPC, with or without SAL or a given analogue at concentrations based on efficacy results obtained as disclosed above. A peristaltic pump will supply fresh SMHB containing SAL and remove exhausted media from the model at a half-life equivalent to 6 hr for the vancomycin experiments and 9 r for the daptomycin experiments, as above.

Modeling the Impact of SALs on Target Gene Modulation in MRSA from Distinct Tissue Contexts. Of great interest will be to define the impact of SAL or its analogues alone and combined with vancomycin or daptomycin on S. aureus target gene expression in fluid versus tissue contexts ex vivo. To do so, organisms will be isolated from the two distinct contexts simulated in the ex vivo model of IE: 1) circulating organisms from the chamber compartment fluid, simulating persistent bacteremia; such organisms represent planktonic members of the overall cell population, and are typically of low density and in logarithmic phase growth; and 2) organisms buried deep within evolving SEVs, representing sessile members of the population.

Importantly, such cells often comprise high-density microcolonies which have considerably different metabolic and/or growth features than planktonic cells. Moreover, such microcolonies are prone to biofilm formation as described in Proctor et al. Nature [Rev Micro]. 2006 (4):295-305. Further, these conditions foster stationary phase growth and phenotypic switching to small-colony variant morphotypes, Proctor et al. Nature [Rev Micro]. 2006 (4):295-305. which are most typically less susceptible to peptide antibiotics. For these genotypic assays, we will follow a protocol we have found successful in isolating mRNA from S. aureus organisms in many relevant tissue contexts ex vivo and in vivo. Xiong et al. J Infect Dis. 2006 194:1267-75; Xiong et al. Infect Immun 2004 72:1832-6. Particularly important in this respect is a tissue dissolution method that yields organisms suitable for mRNA extraction in isolation from tissue debris. Thus, organisms will be obtained from chamber fluid and SEV model phases, and processed for qRT-PCR for the genes-of-interest as in Specific Aim 1B. The most interesting outcomes of gene expression in response to SAL-antibiotic combinations can be verified using selected promoter:gfp reporter constructs as we have done previously. Wann et al. J Biol Chem. 2000 275:13863-71; Kupferwasser et al. Circulation. 1999 99:2791-7; Xiong et al. J Infect Dis. 2002 186:668-77; Xiong et al. J Infect Dis. 2006 194:1267-75; Xiong et al. Infect Immun. 2004 72:1832-6.

EXAMPLE VIII

Translation and Optimization of SAL Mitigation of Antibiotic Resistance within a Relevant In Vivo Model of MRSA Endovascular Infection This example demonstrates that PK-PD parameters crucial to the beneficial effects of SAL on antibiotic efficacy or resistance in vitro and ex vivo will be pharmacologically achievable in vivo; and 2) the salutary effects of SAL will manifest in distinct target tissue contexts and temporal phases of infection in vivo. Crucial to testing these hypotheses will be use of a discriminative in vivo IE model that reflects distinct establishment, progression, and dissemination phases of infection in blood and multiple target organs, and host factors in each context. These factors may further influence the extent or duration to which SAL-antibiotic combinations exert their net synergistic effects. Thus, the IE studies below will optimize the beneficial impact of SAL on vancomycin or daptomycin efficacy and resistance in the context of whole animal PK-PD profiles in vivo.

The efficacious anti-MRSA PK-PD relationships of vancomycin or daptomycin plus SAL that mitigate antibiotic resistance will be applied in vitro and ex vivo into the IE model; and the role of SAL on the net efficacy of vancomycin and daptomycin in MRSA infection of multiple target organ systems in the IE model will be optimized (target tissues to be evaluated will include blood, vegetations, and kidneys); and the impact of SAL on the genotypic correlates of vancomycin and daptomycin efficacy versus resistance in the above target organs in the IE model in vivo.

The benefits of SAL-antibiotic combinations as modeled in vitro and ex vivo will be translated into optimally efficacious outcomes using adjunctive SAL-vancomycin or -daptomycin therapy against MRSA. Results will not only refine in vitro and ex vivo models, but lay the groundwork for pre-clinical and clinical studies to evaluate novel combined SAL-antibiotic regimens in treating human MRSA infections. Translational approaches such as these are an essential bridge to improved treatment of life threatening MRSA infections.

Rabbit IE is a well-characterized model for the in vivo evaluation of S. aureus gene regulatory pathways, net virulence and antibiotic responses as described by Xiong et al. Infect Immun. 2004 72:1832-6; Weidenmaier et all. Infect Immun 2005 73:8033-8; Dhawan et al. Antimicrob Agents Chemother. 2000 44:3206-9; Bayer et al. Infect Immun. 1997 65:4652-60; Cheung et al. J Clin Invest. 1994 94:1815-22; Weidenmaier et al. J Infect Dis. 2005 191:1771-7. This model is viewed as a "gold standard" for such evaluations, as it closely mimics its human counterpart microbiologically, immunologically, histopathologically, pathogenically and anatomically in terms of organ involvement as described in Xiong et al. J Infect Dis. 2006 194:1267-75; Xiong et al. Infect Immun. 2004 72:1832-6; van Wamel et al. Microb Pathog. 2002 33:73-9. Moreover, the model represents a composite of acute (bacteremia) and subacute infection (target organ abscesses), accompanied by high target tissue microbial densities (e.g. $\geq 10^5$-$10^8$ CFU/gm) as described by Xiong et al. J Infect Dis. 2006 194:1267-75; Xiong et al. Infect Immun. 2004 72:1832-6. Therefore, it is an ideal model system to uantify the in vivo effects of SAL on antibiotic efficacy and resistance that are key to our central hypotheses.

The IE model involves the placement of a polyethylene catheter retrograde via the right carotid artery in anesthetized animals, across the aortic valve, into the left ventricular apex, where it remains indwelling as described by Xiong et al. Infect Immun 2004 72:1832-6; Yeaman M R, Bayer A S. *Staphylococcus aureus*, platelets, and the heart. Curr Infect Dis Rep. 2000 2:281-298; Yeaman et al. Handbook of Animal Models of Infection. Academic Press, New York, N.Y. Catheter trauma of valvular and mural endocardium results in development of platelet- and fibrin-rich sterile thrombi ("sterile" vegetations). Subsequent intravenous (iv) inoculation of S. aureus at an $ID_{95}$ inoculum achieves reliable colonization of cardiac vegetations, microbial persistence and proliferation, and vegetation growth. In turn, the infection evolves over time to produce hematogenous seeding of distant target organs (i.e., kidneys, spleen), and re-seeding of endocardial lesions.

Translating Efficacious PK-PD Profiles of SAL-Antibiotic Combinations into a Well-Defined Model of Endovascular MRSA Infection (IE).

The PK and PD of both vancomycin and daptomycin have been well established in rabbit models of IE. Dhawan et al. J Infect Dis. 1999 180:1561-8; Xiong et al. Antimicrob Agents Chemother. 2005 49:380-7. Moreover, the PK of SAL has also been defined in this same model as described by Wann et al. J Biol Chem. 2000 275:13863-71; Kupferwasser et al. Circulation. 1999 99:2791-7. These models will be appied to translate PK-PD exposure strategies that enhance antibiotic efficacy or mitigate resistance into animals with established IE due to the study strains listed in Figure x. Guided by results described in the preceding examples, computer-generated PK-PD modeling as described by Tam et al. J Infect Dis. 2007

195:1818-27; Drusano et al. Clin Infect Dis. 2006 42:525-32; Gumbo et al. J Infect Dis. 2004 190:1642-51, will be used to design a series of SAL-antibiotic dosing strategies that will mirror and encompass regimens identified as enhancing efficacy and/or minimizing resistance emergence. Moreover, such modeling will also address "humanized" dosing regimens modeled to minor human PK-PD in the rabbit. Together, these approaches will determine relevant and achievable dosing strategies to evaluate SAL-antibiotic synergy. For in vivo studies, SAL will be administered in the form of the parent compound, aspirin, as this is available in an iv formulation, while SAL is not.

A logical algorithm will be followed for the experiments described herein: 1) three *S. aureus* strains identified in Aims 1 and 2 to exhibit SAL-modulated phenotypic and/or genotypic resistance determinants will be prioritized for the Aim 3 studies. Included within this panel will be one VSSA/DSSA, one VISA and one DNSA strain (FIG. 13), representing the gamut of peptide antibiotic susceptibilities commonly seen in clinical strains; 2) SAL-antibiotic regimens with the greatest combined efficacy and mitigation of resistance will be prioritized for testing and; 3) in addition, at least one regimen will be prioritized that does not have such impacts on efficacy or resistance in vitro or ex vivo; this will account for the possibility that host factors may positively enhance PK-PD outcomes over and above those documented in the in vitro and ex vivo studies. This algorithm will provide definitive and hypothesis-driven results.

Evaluating SAL-Antibiotic Regimens to Optimize Net Efficacy and/or Mitigate Resistance: Animals with established IE will be randomized to six treatment groups: i) untreated controls; ii) aspirin alone; iii) daptomycin alone; iv) vancomycin alone; v) aspirin-vancomycin in combination; and yl) aspirin-daptomycin in combination. The aspirin-alone group is included, as we have previously shown such treatment has modest salutary activity on IE progression in this model as described by Palma et al. J Bacteriol. 2006 188:5896-903; Wann et al. J Biol Chem. 2000 275:13863-71; Kupferwasser et al. Circulation. 1999 99:2791-7. As indicated above, within each treatment group, several sub-groups will be established in which animals will receive computer-generated drug protocols designed to achieve regimens that are predicted to: a) have maximal efficacy and resistance suppression; b) have minimal efficacy but suppress resistance; and/or c) have minimal efficacy and foster emergence of resistance. Based on in vitro I ex vivo PK-PD observations, we will use computer-generated mathematical modeling to accurately estimate PK-PD parameters needed for in vivo efficacy in humans as described by Tam et al. J Infect Dis. 2007 195:1818-27; Drusano et al. Clin Infect Dis. 2006 42:525-32; Gumbo et al. J Infect Dis. 2004 190:1642-51. All treatment groups will receive 7d of therapy to maximize the opportunity for antibiotic resistance to emerge. All agents will be administered iv; once/day for aspirin and daptomycin, and twice/day for vancomycin. Based on statistical modeling, 10 animals will be included in each of three treatment subgroups. We have calculated that such group sizes will optimize statistical comparisons among groups, with an 80% power at the P<0.05 level. Therefore, for each strain assessed, we estimate an overall use of ~160 animals. This number of animals will also account for a surgical-related mortality of ~5% in this model, while yielding a statistically-relevant sample size.

To define AUC:MIC ratios for each therapeutic regimen, animals will have serial blood samples taken over the first 24 hr (time points: 0; 1; 2; 4; 8; 16; and 24 hr) to determine drug levels, including SAL. Quantitative assays will be done as detailed above. The timing of the samples is predicated on the relatively long half-life of each study agent. Such sampling will enable calculation of an AUC:MIC ratio for each of the administered regimens, and correlation of these ratios with primary outcomes of net efficacy and mitigation of resistance emergence.

Quantifying Efficacy of SAL-Antibiotic Regimens: At 24 h after the last drug dose (7d) of treatment, all animals undergo sacrifice. Blood, cardiac vegetations, and kidneys will be aseptically excised and processed for quantitative culture as previously described. Along with standard plating methods, all blood and tissue samples will be parallel plated on solid media containing daptomycin or vancomycin at 3× or 6× the MIC of the inoculum strain to detect potential in vivo development of drug resistance in animals treated with the respective agent. The MICs of representative resistant isolates will be determined, and resistance ratios then calculated from the difference between the number of organisms overall in the target tissue-of-interest vs. the umber growing on antibiotic-containing plates. Statistical analyses will be similar to those described below.

Assessing the Impact of SAL Regimens on Genotypic Correlates of Antibiotic Resistance in Isolates from Distinct Target Organs in the IE Model. As an important correlate of any antibiotic treatment outcome above, target gene expression profiles will be determined to assess the influence of SAL regimens on resistance, virulence, or regulatory genes-of-interest. As for in vitro and ex vivo studies above, quantitative RT-PCR will be performed to query gene expression in target tissues in IE. Guided by the preceding experiments, the studies will prioritize a consensus set of genes for query that correlates with the development of vancomycin and/or daptomycin resistance. This set will represent those genes most frequently correlated with resistance emergence for the strain set used above. For each strain selected for use, no more than 4 target genes will be selected from the candidate list in FIG. 11. If possible, target gene sets will include at least one antibiotic resistance, one adhesin, one toxin, and one regulatory gene, to encompass a prototype cluster of genes found to modulate efficacy and/or resistance emergence. The qRT-PCR techniques used above will be applied to isolated target tissues for gene expression. To verify key results, a promoter:gfp reporter fusion system can be used to monitor selected target gene expression in vivo. We have engineered GFP-reporter constructs for numerous genes-of-interest in prior IE studies (e.g., agr RNAIII, cap5 and cap 8, sarA and fnbA) as described by Palma et al. J Bacteriol. 2006 188:5896-903; Wann et al. J Biol Chem. 2000 275:13863-71; Kupferwasser et al. Circulation. 1999 99:2791-7; Xiong et al. J Infect Dis. 2002 186:668-77; Xiong et al. J Infect Dis. 2006 194:1267-75; Xiong et al. Infect Immun. 2004 72:1832-6. It is feasible to transfect such reporter plasmids into study strains using well-established techniques.

To assess MRSA genotypic correlates of SAL-antibiotic outcomes, treatment protocols identical to those above in the six treatment groups will be followed, but modified to sacrifice one group of animals early in the infection course (day 1 of infection; pretreatment) and one group late in the treatment course (day 7—time of sacrifice; post-treatment). At time of sacrifice, blood and tissue bacterial cells will be processed for qRT-PCR profiling as above to quantify gene expression profiles. This strategy will enable definitive evaluation of: 1) the temporal profile of gene expression as a correlate of optimal efficacy and minimal resistance emergence; and 2) target tissue-specific relationships on these relationships. All gene expression profiles in treatment groups will be compared to the temporal evolution of gene expression in untreated control animals. Based on sample-size calculations above, and two separate sacrifice time-points, we project that a total of ~160 animals strain will be required.

The above experiments 1) define the SAL-antibiotic regimens that optimize net anti-staphylococcal efficacy in vivo; 2) define SAL-antibiotic regimens that minimize resistance emergence in vivo; 3) discern the key AUC:MIC relationships that optimize these first two goals; and 4) adjudicate whether specific PK-PD relationships are relevant to these goals in distinct target tissues within different microenvironments.

The above experiments further provide target tissue-specific assessment of optimal PK-PD strategies for SAL-antibiotic combinations to enhance efficacy and minimize resistance emergence in a relevant MRSA infection model; and 2) correlation of these phenotypic outcomes with expression profiles of candidate genes involved in peptide antibiotic resistance, virulence, and regulation thereof. These outcomes will optimize the beneficial impact of SAL on vancomycin and daptomycin efficacy and resistance in context of actual PK-PD profiles in vivo.

Analysis of experimental data will be performed using standard methods, including analysis of variance with Tukey's test for multiple comparisons of significance for continuous data sets. We will use Chi-square or Fisher's Exact Test to evaluate proportional data sets. In selected studies, the time required to achieve 99.9% killing will be determined by linear regression, and potential differences in survival of distinct animal groups will be assessed by Kaplan-Meier survival test. P values <0.05 will be considered significant.:

As shown herein, SALs favorably modulate expression of the MRSA resistome and virulon to enhance anti-MRSA efficacy. Disclosed herein are in vitro, ex vivo and in vivo studies that support the therapeutic outcomes against invasive MRSA infections. This invention provides methods of adjunctive SAL-peptide antibiotic therapy to mitigate resistance and improve outcomes of life-threatening invasive MRSA infections in humans.

EXAMPLE IX

Modulation of Virulence Gene Expression in *Staphylococcus aureus* Using Salicylate Analogues This example demonstrates that SAL and DIF significantly modulate regulatory and VF gene expression in MSSA and MRSA.

Figure 18:
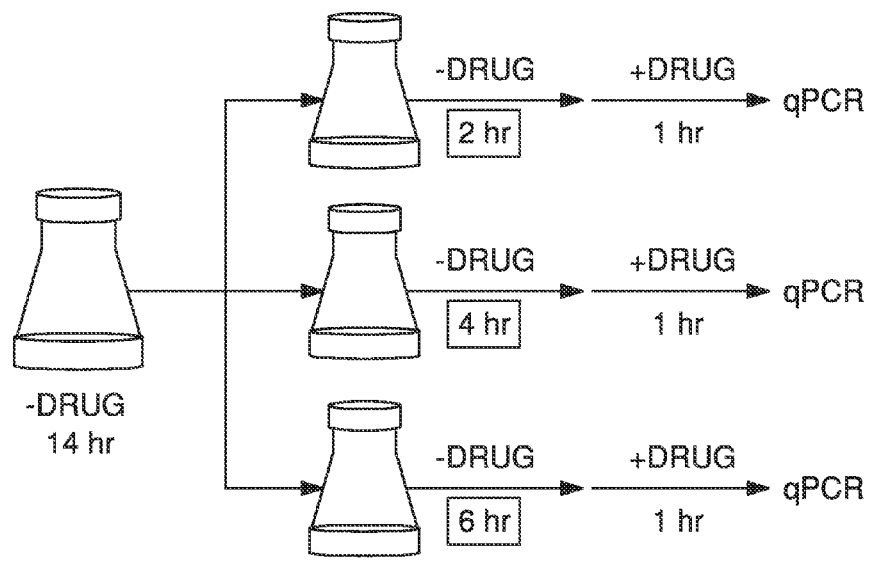
FIG. 18 shows the experimental design for Example 12.
Figure 19:
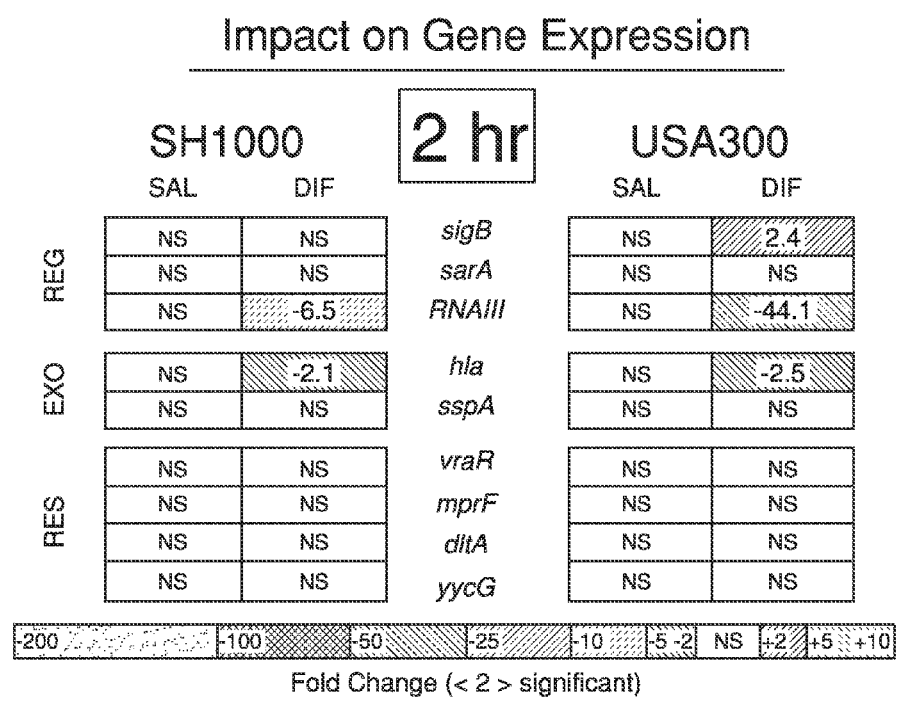
FIG. 19 shows that the impact of SAL and DIF on gene expression in S. aureus strains SH1000 and USA300 2 hours into the log phase.
Figure 20:
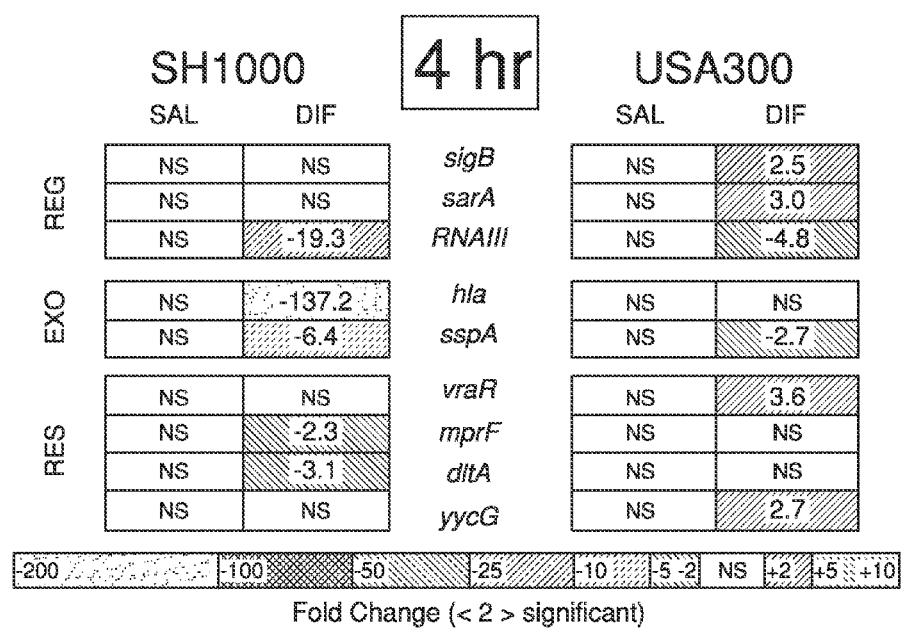
FIG. 20 shows that the impact of SAL and DIF on gene expression in S. aureus strains SH1000 and USA300 4 hours into the log phase.
Figure 21:
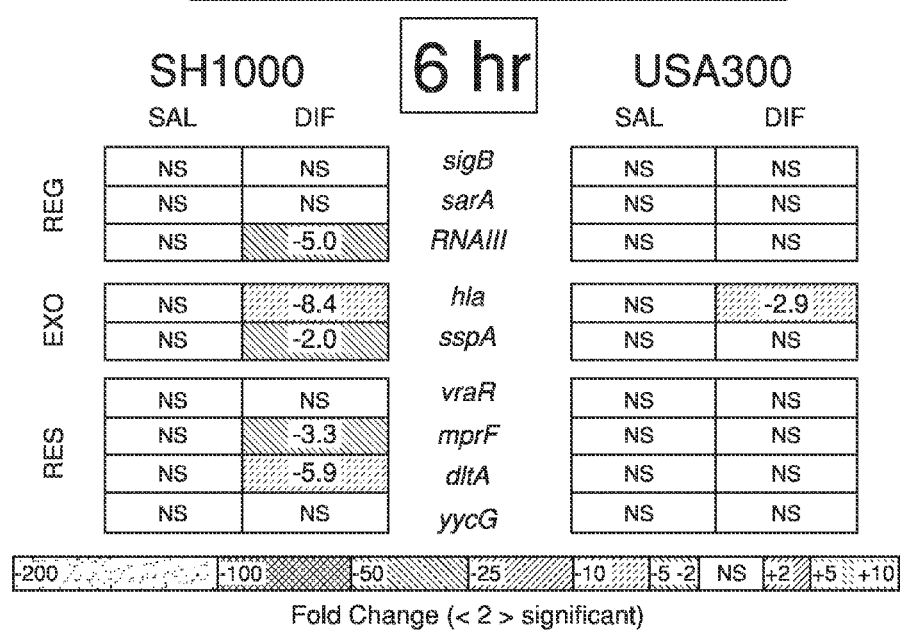
FIG. 21 shows that the impact of SAL and DIF on gene expression in S. aureus strains SH1000 and USA300 6 hours into the log phase.
Figure 22:
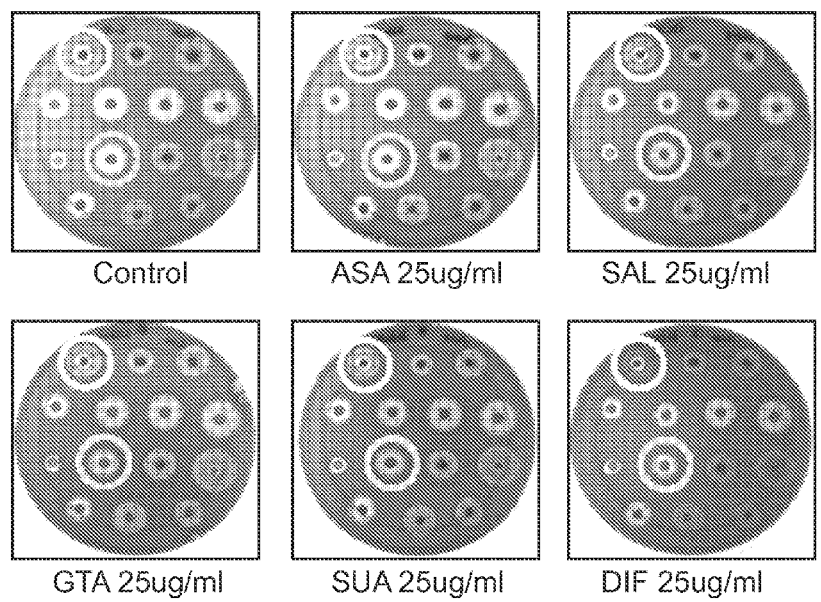
FIG. 22 shows the impact of ASA, SAL, GTA, SUA and DIF on hemolysis in S. aureus.
Figure 24:
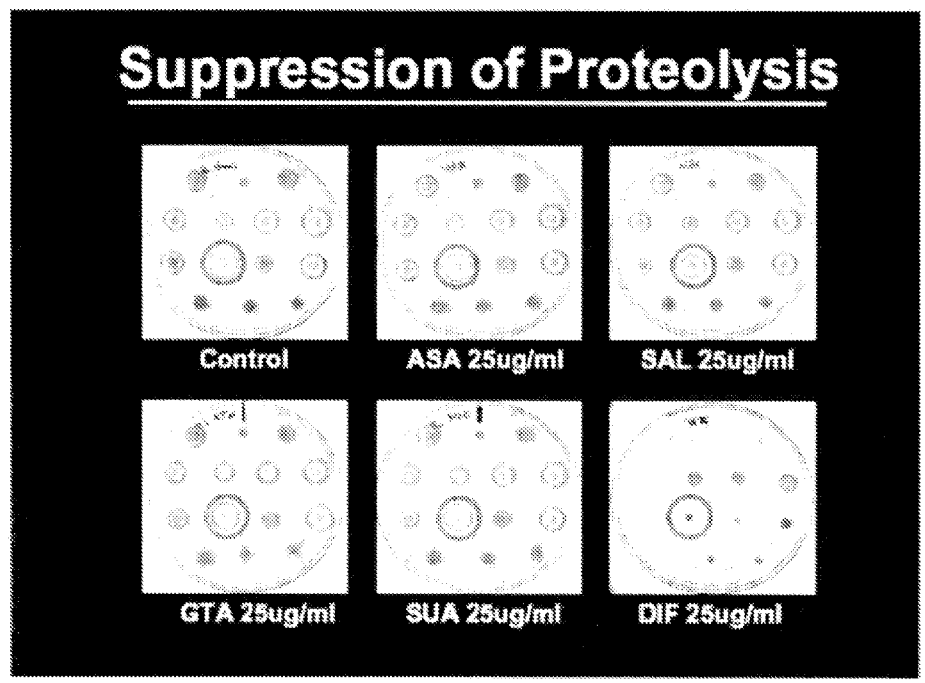
FIG. 24 shows the impact of ASA, SAL, GTA, SUA and DIF on proteolysis in S. aureus.

As shown in FIGS. 19-21, modulation of gene regulation occurs early in log phase (2-6 hr) USA300, USA300, one of the more virulent community-associated methicillin-resistant *Staphylococcus aureus* (MRSA) strains showed vulnerability <6 hr; while SH1000 had longer vulnerability. The experimental design is shown in FIG. 18.

DIF showed a ten-fold higher reduction than SAL of RNAIII (agr), hla, sspA.

Phenotypic data obtained for the strains shown in FIG. 21 showed that the effects are not background specific; however, specific regulatory genes/loci are involved.•

Figure 26:
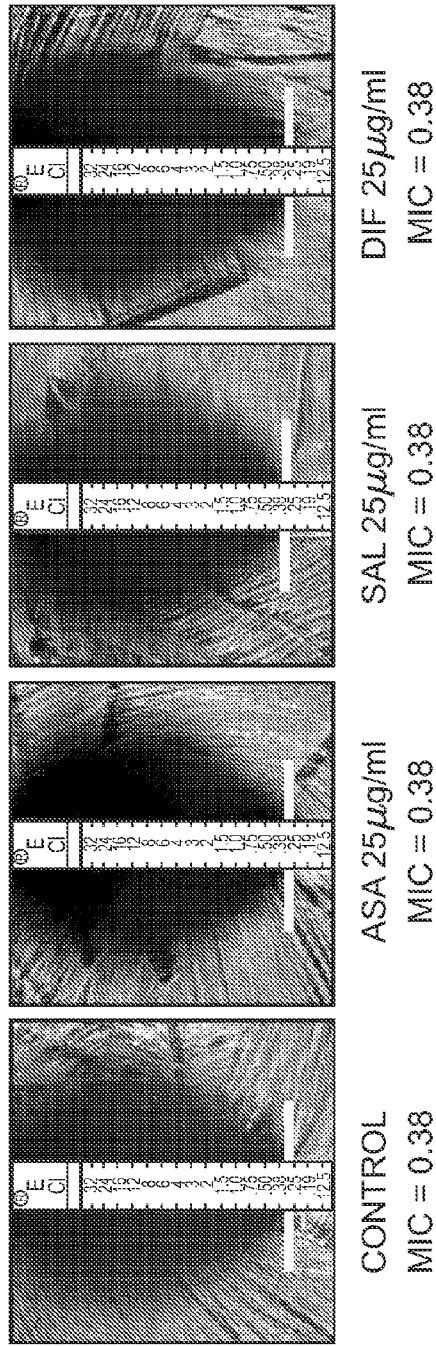
FIG. 26 shows the impact of ASA, SAL and DIF on antibiotic minimum inhibitory concentrations (MICs).

The salicylate analogs showed no detectable change in antibiotic MICs at clinical levels as shown in FIG. 26.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for preventing or treating an infection caused by a microorganism, said method comprising systemically administering to a subject in need thereof a therapeutically effective amount of a salicylic acid (SAL) analogue comprising one or more halogenated phenyl moieties, wherein said subject has an infection caused by a microorganism.

2. The method of claim 1, wherein the microorganism is a species of the bacterial genus *Staphylococcus*.

3. The method of claim 2, wherein said species is *Staphylococcus aureus*.

4. The method of claim 1, wherein said microorganism is a strain that is resistant to at least one antibiotic.

5. The method of claim 4, wherein said strain is methicillin-resistant *Staphylococcus aureus* (MRSA).

6. The method of claim 1, wherein said SAL analogue is Diflunisal.

7. A method for preventing or treating an infection caused by methicillin-resistant *Staphylococcus aureus* (MRSA), comprising systemically co-administering to a subject in need thereof therapeutically effective amounts of a salicylic acid (SAL) analogue comprising one or more halogenated phenyl moieties and at least one additional antimicrobial agent, where said SAL analogue and said at least one additional antimicrobial agent are co-administered individually or collectively, and wherein said subject has an infection caused by MRSA.

8. The method of claim 7, wherein said additional antimicrobial agent is vancomycin, daptomycin or linezolid.

9. The method of claim 7, wherein said SAL analogue is Diflunisal.

10. A method for preventing or treating an infection caused by vancomycin-resistant enterococci (VRE), comprising systemically co-administering to a subject in need thereof therapeutically effective amounts of a salicylic acid (SAL) analogue comprising one or more halogenated phenyl moieties and at least one additional antimicrobial agent, where said SAL analogue and said at least one additional antimicrobial agent are co-administered individually or collectively, and wherein said subject has an infection caused by VRE.

11. The method of claim 10, wherein said additional antimicrobial agent is linezolid.

12. The method of claim 10, wherein said SAL analogue is Diflunisal.

13. The method of claim 5, wherein said MRSA stain is vancomycin susceptible (VSSA), vancomycin-intermediate susceptible (VISA) or vancomycin-resistant (VRSA).

14. The method of claim 1, wherein said infection is an acute infection.

15. The method of claim 7, wherein said infection is an acute infection.

16. The method of claim 10, wherein said infection is an acute infection.

* * * * *